(12) United States Patent
Anzalone et al.

(10) Patent No.: US 12,715,852 B2
(45) Date of Patent: Aug. 25, 2026

(54) PREPARATION OF OPTICALLY ACTIVE ENANTIOMERS OF PIPERONYL AMINES BY RESOLUTION OF THE DIASTEREOMERIC SALTS

(71) Applicant: EmpathBio, Inc., Encinitas, CA (US)

(72) Inventors: Luigi Anzalone, Hull, MA (US); Nicholas Morra, Ontario (CA); Majed Fawaz, Foxborough, MA (US)

(73) Assignee: EmpathBio, Inc., New York, NY (US)

( * ) Notice: Subject to any disclaimer, the term of this patent is extended or adjusted under 35 U.S.C. 154(b) by 753 days.

(21) Appl. No.: 17/946,406

(22) Filed: Sep. 16, 2022

(65) Prior Publication Data

US 2023/0109467 A1 Apr. 6, 2023

Related U.S. Application Data

(60) Provisional application No. 63/245,496, filed on Sep. 17, 2021.

(51) Int. Cl.
*C07D 317/06* (2006.01)

(52) U.S. Cl.
CPC .................................. *C07D 317/06* (2013.01)

(58) Field of Classification Search
None
See application file for complete search history.

(56) References Cited

U.S. PATENT DOCUMENTS 3,907,864 A 9/1975 Biel et al.
4,017,636 A 4/1977 Jones et al.
4,937,360 A 6/1990 Liu et al.
5,061,727 A 10/1991 Bloom et al.
5,861,426 A 1/1999 Del Soldato et al.
5,932,749 A 8/1999 Li et al.
6,436,950 B1 8/2002 Achari et al.
7,048,545 B2 5/2006 McClusky
9,878,992 B2 1/2018 Bhamidipati et al.
9,907,812 B2 3/2018 Bapat et al.
10,000,555 B2 6/2018 Doronina et al.
11,414,423 B1 8/2022 Olson et al.
11,845,736 B2 12/2023 Rao et al.
11,912,680 B2 2/2024 Perni et al.
11,958,821 B2 4/2024 Clark
11,993,577 B2 5/2024 Fawaz et al.
12,221,428 B2 2/2025 Cozzi et al.
12,365,661 B2 7/2025 Baggott
12,454,516 B2 10/2025 Perni
12,492,178 B2 12/2025 Fawaz et al.
2003/0171303 A1 9/2003 Gallop et al.
2003/0207884 A1 11/2003 Haap et al.
2005/0130244 A1 6/2005 Zheng et al.
2006/0035863 A1 2/2006 Barbeau
2006/0205779 A1 9/2006 Mu et al.
2006/0205946 A1 9/2006 Ji et al.
2007/0027208 A1 2/2007 Caron et al.
2008/0045588 A1 2/2008 Gant et al.
2008/0146567 A1 6/2008 Kolczewski et al.
2008/0293695 A1 11/2008 Bristol et al.
2009/0111741 A1 4/2009 Aldrich et al.
2009/0131516 A1 5/2009 Mickle et al.
2009/0143408 A1 6/2009 Eissenstat et al.
2010/0137428 A1 6/2010 Bozzoli et al.
2013/0317020 A1 11/2013 Ruah et al.
2014/0243544 A1 8/2014 Wang et al.
2018/0243241 A1 8/2018 Popp et al.
2018/0344728 A1 12/2018 Bosse et al.
2020/0369707 A1 11/2020 Verhoeven et al.
2021/0113559 A1 4/2021 Boss et al.
2021/0145851 A1 5/2021 Stamets
2021/0332012 A1 10/2021 Olson et al.
2021/0346341 A1 11/2021 Liechti
2022/0151986 A1 5/2022 Liechti et al.
2022/0267252 A1 8/2022 Trachsel et al.
2022/0354822 A1 11/2022 Barrow et al.
2023/0096116 A1 3/2023 Fawaz et al.
2023/0097530 A1 3/2023 Short et al.
2023/0113351 A1 4/2023 Blumstock et al.
2023/0129723 A1 4/2023 Short et al.
2023/0150965 A1 5/2023 Duncton et al.
2023/0150966 A1 5/2023 Duncton et al.

(Continued)

FOREIGN PATENT DOCUMENTS

AU 2018268311 B2 2/2022
CN 101822841 A 9/2010

(Continued)

OTHER PUBLICATIONS

Challener, C.A., Chiral Resolution with and without Resolving Agents. Pharmaceutical Technology, 2015, 39, p. 1-9.*
Sakai et al., Novel Optical Resolution Technologies. Topics in Current Chemistry, 2007, 269. p. 1-313.*
Acquas, E., et al., "Differential effects of intravenous R,S-(+/−)-3,4-methylenedioxymethamphetamine (MDMA, Ecstasy) and its S(+)- and R(−)-enantiomers on dopamine transmission and extracellular signal regulated kinase phosphorylation (pERK) in the rat nucleus accumbens shell and core", Journal of Neurochemistry, 2007, vol. 102, pp. 121-132.

(Continued)

*Primary Examiner* — Po-Chih Chen

(74) *Attorney, Agent, or Firm* — COOLEY LLP

(57) ABSTRACT

Provided herein is a process for resolving the (S)- and (R)-enantiomers of a compound of Formula (I), wherein L, $R^1$, and $R^2$ are defined herein.

(I)

22 Claims, No Drawings

(56) References Cited

U.S. PATENT DOCUMENTS

2023/0181521 A1 6/2023 Duncton et al.
2023/0202998 A1 6/2023 Duncton et al.
2023/0227420 A1 7/2023 Rao et al.
2023/0227421 A1 7/2023 Perni et al.
2023/0227422 A1 7/2023 Duncton et al.
2023/0278977 A1 9/2023 Fawaz et al.
2023/0310368 A1 10/2023 Barrow et al.
2023/0416219 A1 12/2023 Schneider et al.
2024/0082212 A1 3/2024 Short et al.
2024/0208920 A1 6/2024 Fawaz et al.
2024/0217944 A1 7/2024 Fawaz
2024/0285577 A1 8/2024 Nair et al.
2024/0327371 A1 10/2024 Clark
2024/0335418 A1 10/2024 Obidin et al.
2024/0342126 A1* 10/2024 Slassi ..................... A61K 47/10
2024/0400532 A1 12/2024 Perni
2024/0408054 A1 12/2024 Short et al.
2024/0409526 A1 12/2024 Clark
2024/0425470 A1 12/2024 Khan et al.
2025/0026731 A1 1/2025 Rao et al.
2025/0034105 A1 1/2025 Duncton et al.
2025/0152553 A1 5/2025 Khan et al.
2025/0205191 A1 6/2025 Rao et al.
2026/0028324 A1 1/2026 Perni et al.
2026/0055075 A1 2/2026 Fawaz et al.

FOREIGN PATENT DOCUMENTS

CN 110294789 A 10/2019
DK 3271357 T3 2/2020
EP 2687854 A1 1/2014
NZ 239929 A 12/1994
WO WO-2004004648 A2 1/2004
WO WO-2005019163 A2 3/2005
WO WO-2005038049 A2 4/2005
WO WO-2007090733 A1 8/2007
WO WO-2008033351 A2 3/2008
WO WO-2008046135 A1 4/2008
WO WO-2009049233 A1 4/2009
WO WO-2009089494 A2 7/2009
WO WO-2009095479 A2 8/2009
WO WO-2012177986 A2 12/2012
WO WO-2013088255 A1 6/2013
WO WO-2014013063 A1 1/2014
WO WO-2014139161 A1 9/2014
WO WO-2016148306 A1 9/2016
WO WO-2017147375 A1 8/2017
WO WO-2018210988 A1 11/2018
WO WO-2019018584 A1 1/2019
WO WO-2020077217 A1 4/2020
WO WO-2020101543 A1 5/2020
WO WO-2020252384 A1 12/2020
WO WO-2021252538 A2 12/2021
WO WO-2022006192 A1 1/2022
WO WO-2022010937 A1 1/2022
WO WO-2022032147 A1 2/2022
WO WO-2022053696 A1 3/2022
WO WO-2022061242 A1 3/2022
WO WO-2022069690 A2 4/2022
WO WO-2022106947 A1 5/2022
WO WO-2022150525 A1 7/2022
WO WO-2022182602 A2 9/2022
WO WO-2022232948 A1 11/2022
WO WO-2022235530 A1 11/2022
WO WO-2022251690 A1 12/2022
WO WO-2022256720 A2 12/2022
WO WO-2023283373 A1 1/2023
WO WO-2023283386 A2 1/2023
WO WO-2023019369 A1 2/2023
WO WO-2023034510 A1 3/2023
WO WO-2023044027 A1 3/2023
WO WO-2023056102 A1 4/2023
WO WO-2023056472 A1 4/2023
WO WO-2023081895 A1 5/2023
WO WO-2023081897 A1 5/2023
WO WO-2023081899 A1 5/2023
WO WO-2023092044 A2 5/2023
WO WO-2023129958 A2 7/2023
WO WO-2023131841 A1 7/2023
WO WO-2023250247 A2 12/2023
WO WO-2024052880 A1 3/2024
WO WO-2024054279 A1 3/2024
WO WO-2024102845 A2 5/2024
WO WO-2024145663 A2 7/2024
WO WO-2024148267 A1 7/2024
WO WO-2024166057 A1 8/2024
WO WO-2024166058 A1 8/2024
WO WO-2024166059 A1 8/2024
WO WO-2024254411 A2 12/2024
WO WO-2024254505 A2 12/2024
WO WO-2025010308 A2 1/2025
WO WO-2025096895 A1 5/2025
WO WO-2025137563 A1 6/2025

OTHER PUBLICATIONS

Anderson et al., "Absolute configuration and psychotomimetic activity", NIDA Res Monogr. 1978, vol. (22), pp. 8-15.

Green et al., "The pharmacology and clinical pharmacology of 3,4-methylenedioxymethamphetamine (MDMA, "ecstasy")", Pharmacol Rev, Sep. 2003; 55(3): 463-508. Epub Jul. 17, 2003.

Kozma, et al., Optical resolution of N-methylamphetamine via diastereoisomeric salt formation with 2R, 3R-O, O'-di-p-toluoyltartaric acid. Chirality: The Pharmacological, Biological, and Chemical Consequences of Molecular Asymmetry, 1999, pp. 373-375.

Nichols, et al., Derivatives of 1-(1, 3-benzodioxol-5-yl)-2-butanamine: representatives of a novel therapeutic class, Journal of Medicinal Chemistry, Oct. 1986, pp. 2009-2015.

United States Patent and Trademark Office, International Search Report and Written Opinion for PCT/US2022/043833, Jan. 12, 2023, 13 pages.

Baker, et al., Critical evaluation of methodology commonly used in sample collection, storage and preparation for the analysis of pharmaceuticals and illicit drugs in surface water and wastewater by solid phase extraction and liquid chromatography-mass spectrometry, Journal of Chromatography A, 2011, pp. 8036-8059.

Baker, et al., Drugs of abuse in wastewater and suspended particulate matter—Further developments in sewage epidemiology, Environment International, 2012, pp. 28-38.

Baker, et al., Multi-residue analysis of drugs of abuse in wastewater and surface water by solid-phase extraction and liquid chromatography—positive electrospray ionisation tandem mass spectrometry, Journal of Chromatography A, 2011, pp. 1620-1631.

Baker, et al., Multi-residue determination of the sorption of illicit drugs and pharmaceuticals to wastewater suspended particulate matter using pressurized liquid extraction, solid phase extraction and liquid chromatography coupled with tandem mass spectrometry, Journal of Chromatography A, Nov. 2011, pp. 7901-7913.

Barreiro, J.C., et al., "A High-Resolution Magic Angle Spinning NMR Study of the Enantiodiscrimination of 3,4-Methylenedioxymethamphetamine (MDMA) by an Immobilized Polysaccharide-Based Chiral Phase", PLoS ONE, vol. 11, No. 9, Sep. 26, 2016, pp. 1-11.

Castrignano, et al., Enantiomeric profiling of chiral drug biomarkers in wastewater with the usage of chiral liquid chromatography coupled with tandem mass spectrometry, Journal of chromatography A, Mar. 2016, pp. 84-99.

Castrignano, et al., Enantiomeric profiling of chiral illicit drugs in a pan—European study, Water Research, Mar. 2017, 56 pages.

Chen, et al., Investigation of the relationship between phenol ionization and affinity of norepinephrine for adrenergic receptors using ring-fluorinated analogs, Medicinal Chemistry Research, 1994, pp. 589-597.

Chen, et al., Syntheses of 2,5- and 2,6-difluoronorepinephrine, 2,5-difluoroepinephrine, and 2,6-difluorophenylephrine: effect of disubstitution with fluorine on adrenergic activity, Journal of Medicinal Chemistry, 1993, pp. 3947-3955.

(56) References Cited

OTHER PUBLICATIONS

Clouting, H., "The Commercial Chemistry of MDMA: From Research to Patient Access," MAPS Bulletin Special Edition, Spring 2020, pp. 8-10.
Collins, et al., Identification and characterization of N-tert-butoxycarbonyl-MDMA: a new MDMA precursor, Drug Testing and Analysis, Mar. 2017, pp. 399-404.
Corkery, et al., Deaths in the Lesbian, Gay, Bisexual and Transgender United Kingdom Communities Associated with GHB and Precursors, Current drug metabolism, Nov. 2018, pp. 1086-1099.
Crean, R.D., et al., "Oral Administration of (±)3,4-Methylenedioxymethamphetamine and (+) Methamphetamine Alters Temperature and Activity in Rhesus Macaques", Pharmacol Biochem Behav, vol. 87, No. 1, Authors Manuscript PMC May 1, 2008, pp. 1-18.
Curry et al., "Separating the agony from ecstasy: R(−)-3,4-methylenedioxymethamphetamine has prosocial and therapeutic-like effects without signs of neurotoxicity in mice," Neuropharmacology. Jan. 2018 ; 128: 196-206, 26 pages.
Deluca, et al., Searching the Internet for drug-related web sites: analysis of online available information on ecstasy (MDMA), American Journal on Addictions, Nov. 2007, 5 pages.
Eiden, et al., VMAT2: a dynamic regulator of brain monoaminergic neuronal function interacting with drugs of abuse, Ann N Y Acad Sci., Jan. 2011, pp. 86-98.
Fallon et al., "Stereospecific Analysis and Enantiomeric Disposition of 3,4-Methylenedioxymethamphetamine (Ecstasy) in Humans," Clinical Chemistry (1999) 45:7, 1058-1069.
Fantegrossi, et al., 3, 4-Methylenedioxymethamphetamine (MDMA, "ecstasy") and its stereoisomers as reinforcers in rhesus monkeys: serotonergic involvement, Psychopharmacology, Jun. 2002, pp. 56-64.
Fantegrossi et al., "Pharmacological characterization of the effects of 3,4-methylenedioxymethamphetamine ("ecstasy") and its enantiomers on lethality, core temperature, and locomotor activity in singly housed and crowded mice," Psychopharmacology (2003) 166: 202-211.
Fantegrossi, In vivo pharmacology of MDMA and its enantiomers in rhesus monkeys, Experimental and clinical psychopharmacology, Feb. 2008, 1 page.
Felim et al., "Synthesis and in Vitro Cytotoxicity Profile of the R-Enantiomer of 3,4-Dihydroxymethamphetamine (R-(−)-HHMA): Comparison with Related Catecholamines," Chem. Res. Toxicol. 2010, 23, 211-219.
Filler, et al., Fluorine-containing catecholamines. Synthesis of DL-2,5,6-trifluorodopa, Journal of Fluorine Chemistry, 1981, pp. 483-495.
Fitzgerald, et al., Stereoselective pharmacokinetics of 3, 4-methylenedioxymethamphetamine in the rat, Chirality, 1990, pp. 241-248.
Forsling, et al., The effect of 3,4-methylenedioxymethamphetamine (MDMA,'ecstasy') and its metabolites on neurohypophysial hormone release from the isolated rat hypothalamus, British Journal of Pharmacology, Feb. 2002, pp. 649-656.
Hagele, et al., Enantioselective separation of Novel Psychoactive Substances using a Lux® AMP 3 μm column and HPLC-UV. Journal of Pharmaceutical and Biomedical Analysis, Feb. 2020, 2 pages.
Han, et al., Comparison of the monoamine transporters from human and mouse in their sensitivities to psychostimulant drugs, BMC Pharmacology, Dec. 2006, pp. 1-7.
Heather, E., "The Synthesis and Chemical Profiling of 3,4-Methylenedioxymethamphetamine (MDMA) and Analogues," Thesis, University of Technology Sydney, Oct. 2020, 232 pages.
Hensley, et al., Simultaneous determination of amphetamine, methamphetamine, methylenedioxyamphetamine (MDA), methylenedioxymethamphetamine (MDMA), and methylenedioxyethylamphetamine (MDEA) enantiomers by GC-MS, Journal of Analytical Toxicology, Oct. 1999, pp. 518-523.
Herr, et al., Re-evaluation of the discriminative stimulus effects of lysergic acid diethylamide with male and female Sprague-Dawley rats, Behavioral Pharmacology, Sep. 2020, pp. 776-786.
Hiramatsu, et al., Enantiomeric differences in the effects of 3, 4-methylenedioxymethamphetamine on extracellular monoamines and metabolites in the striatum of freely-moving rats: an in vivo microdialysis study, Neuropharmacology, Mar. 1990, pp. 269-275.
Huot et al., "Characterization of 3,4-Methylenedioxymethamphetamine (MDMA) Enantiomers In Vitro and in the MPTP-Lesioned Primate: R-MDMA Reduces Severity of Dyskinesia, Whereas S-MDMA Extends Duration of ON-Time," The Journal of Neuroscience, May 2011, pp. 7190-7198.
International Search Report and Written Opinion for Application No. PCT/US2022/042353, mailed on Dec. 8, 2022, 9 pages.
International Search Report and Written Opinion for International Application No. PCT/US2022/082468, mailed on Jun. 6, 2023, 11 pages.
Invitation to Pay Fee for International Application No. PCT/US2022/045587 dated Nov. 18, 2022, 3 pages.
Invitation to Pay for International Application No. PCT/US2022/082468 dated Mar. 16, 2023, 2 pages.
Johnson et al., "Effects of the enantiomers of MDA, MDMA and related analogues on [3H]serotonin and [3H]dopamine release from supefused rat brain slices," European Journal of Pharmacology, (1986) 132: 269-276.
Kilpatrick, et al., National estimates of exposure to traumatic events and PTSD prevalence using DSM-IV and DSM-5 criteria, Journal of Traumatic Stress, Oct. 2013, pp. 537-547.
Ladd, et al., Improved synthesis of fluoroveratroles and fluorophenethylamines via organolithium reagents, Journal of Organic Chemistry, 1981, pp. 203-206.
Leapman, et al., Application of parallel recorded EELS to analysis of beam-sensitive organic compounds, Biomed. Eng. Instrum., Proceedings—Annual Meeting, Electron Microscopy Society of America, 1988, pp. 632-633.
Leapman, et al., Applications of electron energy loss spectroscopy in biology: detection of calcium and fluorine, Proceedings—Annual Meeting, Electron Microscopy Society of America, 1982, pp. 412-415.
Liabres et al., "Molecular basis of the selective binding of MDMA enantiomers to the alpha4beta2 nicotinic receptor subtype: synthesis, pharmacological evaluation and mechanistic studies", European Journal of Medicinal Chemistry, Jun. 2014, pp. 35-46.
Madry, et al., Evaluation of drug incorporation into hair segments and nails by enantiomeric analysis following controlled single MDMA intakes, Analytical and Bioanalytical Chemistry, Jan. 2016, pp. 545-556.
Martins, et al., Simultaneous enantioselective determination of amphetamine and congeners in hair specimens by negative chemical ionization gas chromatography—mass spectrometry, Journal of Chromatography B, Oct. 15, 2005, pp. 57-62.
Martins, et al., Time-resolved hair analysis of MDMA enantiomers by GC/MS-NCI, Forensic Science International, Oct. 2007, pp. 150-155.
Mas, et al., Cardiovascular and neuroendocrine effects and pharmacokinetics of 3, 4-methylenedioxymethamphetamine in humans, Journal of Pharmacology and Experimental Therapeutics, Jul. 1, 1999, pp. 136-145.
Matsushima, et al., Optical isomer analysis of 3, 4-methylenedioxyamphetamine analogues and their stereoselective disposition in rats, Journal of Analytical Toxicology, Jan. 1998, pp. 33-39.
Milhazes, et al., Electrochemical and spectroscopic characterisation of amphetamine-like drugs: Application to the screening of 3,4-methylenedioxymethamphetamine (MDMA) and its synthetic precursors, Analytica Chimica Acta, 2007, pp. 231-241.
Murnane, et al., Discriminative stimulus effects of psychostimulants and hallucinogens in S (+)-3, 4-methylenedioxymethamphetamine (MDMA) and R (−)-MDMA trained mice, Journal of Pharmacology and Experimental Therapeutics, Nov. 1, 2009, pp. 717-723.

(56) References Cited

OTHER PUBLICATIONS

Murnane, et al., Endocrine and neurochemical effects of 3, 4-methylenedioxymethamphetamine and its stereoisomers in rhesus monkeys, Journal of Pharmacology and Experimental Therapeutics, Aug. 1, 2010, pp. 642-650.
Murnane, et al., The neuropharmacology of prolactin secretion elicited by 3, 4-methylenedioxymethamphetamine ("ecstasy"): a concurrent microdialysis and plasma analysis study, Hormones and behavior, Feb. 1, 2012, pp. 181-190.
Mustafa, et al., Review Paper: MDMA and the Brain: A Short Review on the Role of Neurotransmitters in Neurotoxicity, Basic and Clinical Neuroscience, 2020, pp. 381-388.
Nair et al., "Fully Validated, Multi-Kilogram cGMP Synthesis of MDMA", ACS Omega, Dec. 20, 2021, vol. 7, 1, pp. 900-907.
Nenajdenko et al., "A new convenient approach to chiral βaryl(heteroaryl)alkylamines," Tetrahedron: Asymmetry (2001) 12: 2517-2527.
Nie, et al., Synthesis of fluorodopamines: effect of aryl fluoro substituents on affinities for adrenergic and dopaminergic receptors, Medicinal Chemistry Research, Jan. 1996, pp. 318-332.
Organic Chemistry Portal "Amino Protecting Groups Stability", (1999), pp. 1-3.
Peters, et al., Concentrations and ratios of amphetamine, methamphetamine, MDA, MDMA, and MDEA enantiomers determined in plasma samples from clinical toxicology and driving under the influence of drugs cases by GC-NICI-MS, Journal of Analytical Toxicology, Nov. 1, 2003, pp. 552-559.
Peters, et al., Drug testing in blood: validated negative-ion chemical ionization gas chromatographic—mass spectrometric assay for determination of amphetamine and methamphetamine enantiomers and its application to toxicology cases, Clinical Chemistry, Sep. 1, 2002, pp. 1472-1485.
Peters, et al., Negative-ion chemical ionization gas chromatography-mass spectrometry assay for enantioselective measurement of amphetamines in oral fluid: application to a controlled study with MDMA and driving under the influence cases, Clinical chemistry, Apr. 1, 2007 A, pp. 702-710.
Pitts et al., (±)-MDMA and its enantiomers: potential therapeutic advantages of R(−)-MDMA, Psychopharmacology, 2018, pp. 377-392.
Pizarro, et al., Stereochemical analysis of 3, 4-methylenedioxymethamphetamine and its main metabolites in human samples including the catechol-type metabolite (3, 4-dihydroxymethamphetamine), Drug Metabolism and Disposition, Sep. 1, 2004, pp. 1001-1007.
Pubchem, SID 235735835, Available Date: Feb. 13, 2015 [retrieved on Apr. 23, 2023], 8 pages. Retrieved from: https://pubchem.ncbi.nlm.nih.gov/substance/235735835.
Pubchem, SID 243280603, Modify Date: Jun. 24, 2015 [retrieved on Dec. 27, 2022, 7 pages. Retrieved: https://pubchem.ncbi.nlm.nih.gov/substance/243280603].
Pubchem, Substance Record for SID 38492237, Dec. 5, 2007, 5 pages.
Pubchem, Substance Record for SID 406789554, Jul. 18, 2020, 6 pages.
Pubchem, Substance Record for SID 439624087, Jan. 15, 2021, 6 pages.
Pubill, et al., Neuronal nicotinic receptors as new targets for amphetamine-induced oxidative damage and neurotoxicity, Pharmaceuticals, Jun. 15, 2011, pp. 822-847.
Rasmussen et al., "Chiral separation and quantification of R/S-amphetamine, R/S-methamphetamine, R/S-MDA, R/S-MDMA, and R/S-MDEA in whole blood by GC-EI-MS," Journal of Chromatography B, (2006) 842: 136-141.
Rickli, et al., Pharmacological profile of novel psychoactive benzofurans, British Journal of Pharmacology, Jul. 2015, pp. 3412-3425.
Rothman, et al., Amphetamine-type central nervous system stimulants release norepinephrine more potently than they release dopamine and serotonin, Synapse, Jan. 1, 2001, pp. 32-41.
Rudnick, et al., The molecular mechanism of "ecstasy" [3, 4-methylenedioxy-methamphetamine (MDMA)]: serotonin transporters are targets for MDMA-induced serotonin release, Proceedings of the National Academy of Sciences, Mar. 1, 1992, pp. 1817-1821.
Schwaninger, et al., Development and validation of LC-HRMS and GC-NICI-MS methods for stereoselective determination of MDMA and its phase I and II metabolites in human urine, Journal of Mass Spectrometry, Jul. 2011, pp. 603-614.
Schwaninger, et al., Stereoselective urinary MDMA (ecstasy) and metabolites excretion kinetics following controlled MDMA administration to humans, Biochemical pharmacology, Jan. 1, 2012, pp. 131-138.
Setola, et al., 3, 4-methylenedioxymethamphetamine (MDMA, "Ecstasy") induces fenfluramine-like proliferative actions on human cardiac valvular interstitial cells in vitro, Molecular Pharmacology, Jun. 1, 2003, pp. 1223-1229.
Steele, et al., Stereochemical effects of 3, 4-methylenedioxymethamphetamine (MDMA) and related amphetamine derivatives on inhibition of uptake of [3H] monoamines into synaptosomes from different regions of rat brain, Biochemical Pharmacology, Jul. 15, 1987, pp. 2297-2303.
Strajhar, et al., Effects of lisdexamfetamine on plasma steroid concentrations compared with d-amphetamine in healthy subjects: A randomized, double-blind, placebo-controlled study, The Journal of steroid biochemistry and molecular biology, Feb. 2019, pp. 212-225.
Substance Record for SID 104098418 to PubChem, Jan. 2011, 6 pages.
Substance Record for SID 117678335 to PubChem, Apr. 2011, 6 pages.
Sun, et al., Facile and universal immobilization of L-lysine inspired by mussels, J. Mater. Chem., 2012, Journal of Materials Chemistry, 2012, pp. 10035-10041.
Thomas, et al., Characterization of 3, 4-methylenedioxypyrovalerone discrimination in female Sprague-Dawley rats, Behavioural Pharmacology, Jul. 2021, pp. 524-532.
Thomsen, et al., In Vitro Drug Metabolism by Human Carboxylesterase 1: Focus on Angiotensin-Converting Enzyme Inhibitors, Drug Metabolism and Disposition, Jan. 2014, pp. 126-133.
Tournier, et al., Interaction of drugs of abuse and maintenance treatments with human P-glycoprotein (ABCB1) and breast cancer resistance protein (ABCG2), International Journal of Neuropsychopharmacology, Aug. 1, 2010, pp. 905-915.
United States Patent and Trademark Office, International Search Report and Written Opinion for International Application No. PCT/US2022/045587 dated Feb. 1, 2023, 25 pages.
United States Patent and Trademark Office, International Search Report and Written Opinion for International Application No. PCT/US2022/077432 dated Dec. 15, 2022, 14 pages.
Verrico, et al., MDMA (Ecstasy) and human dopamine, norepinephrine, and serotonin transporters: implications for MDMA-induced neurotoxicity and treatment, Psychopharmacology, Jan. 2007, pp. 489-503.
Verweij , A., "Impurities in illicit drug preparations; 3,4-methylenedioxyamphetamine and 3-4-methylenedioxymethylamphetamine", Forensic. Sci. Rev., 1992, pp. 1-6.
Weinstock, et al., Ecstasy pill testing: harm minimization gone too far?, Addiction, 2001, pp. 1139-1148.
Weinstock, et al., Synthesis and renal vasodilator activity of some dopamine agonist 1-aryl-2,3,4,5-tetrahydro-1H-3-benzazepine-7,8-diols: halogen and methyl analogs of fenoldopam, Journal of Medicinal Chemistry, 1986, pp. 2315-2325.
Wu, et al., Estimation of tamoxifen metabolite concentrations in the blood of breast cancer patients through CYP2D6 genotype activity score, Breast Cancer Research and Treatment, 2012, pp. 677-683.
Young, et al., MDMA (N-methyl-3,4-methylenedioxyamphetamine) and its Stereoisomers: Similarities and Differences in Behavioral Effects in an Automated Activity Apparatus in Mice, Pharmacol Biochem Behav., Jan. 2008, pp. 318-331.

(56) References Cited

OTHER PUBLICATIONS

Dunlap et al., "Dark Classics in Chemical Neuroscience: 3,4-Methylenedioxymethamphetamine (MDMA)," ACS Chem Neurosci. Oct. 17, 2018; 9(10): 2408-2427, 46 pages.
Levine et al. (editor), "Principles of Forensic Toxicology," Springer, Fifth Edition, 2020, 680 pages.
Lourenco et al., "Chiral separation of 3,4-methylenedioxymethamphetamine (MDMA) enantiomers using batch chromatography with peak shaving recycling and its effects on oxidative stress status in rat liver," Journal of Pharmaceutical and Biomedical Analysis, Jan. 2013, 73:13-17.
Pizarro et al., "Synthesis and Capillary Electrophoretic Analysis of Enantiomerically Enriched Reference Standards of MDMA and its Main Metabolites," Bioorganic & Medicinal Chemistry (2002) 10: 1085-1092.
Angerer et al., "Acute psychotropic, autonomic, and endocrine effects of 5,6-methylenedioxy-2-aminoindane (MDAI) compared with 3,4- methylenedioxymethamphetamine (MDMA) in human volunteers: A self-administration study." Drug Test Anal. Sep. 2024;16(9):1002-1011. doi: 10.1002/dta.3622. Epub Dec. 6, 2023.
Auvelity, (dextromethorphan HBr and bupropion HCI) extended-release tablets, Prescribing Information, Axsome Therapeutics, Inc., 2022, 19 pages.
Bartz, J., et al., "Oxytocin can hinder trust and cooperation in borderline personality disorder." Soc Cogn Affect Neurosci., Oct. 2011; 6(5): 556-63.
Battaglia et al., "Pharmacologic profile of MDMA (3,4-methylenedioxymethamphetamine) at various brain recognition sites." Eur J Pharmacol. Apr. 27, 1988; 149(1-2): 159-63. doi: 10.1016/0014-2999(88)90056-8.
Baumann et al., "Effects of dose and route of administration on pharmacokinetics of (+ or −)-3,4-methylenedioxymethamphetamine in the rat." Drug Metab Dispos. Nov. 2009; 37(11): 2163-70. doi: 10.1124/dmd.109.028506. Epub Aug. 13, 2009.
Berge, S.M., et al., "Pharmaceutical Salts," J. Pharm. Sci., 1977; 66: 1-19.
Biezonski et al., "Effects of a short-course MDMA binge on dopamine transporter binding and on levels of dopamine and its metabolites in adult male rats." Eur J Pharmacol. Feb. 15, 2013; 701(1-3): 176-80. doi: 10.1016/j.ejphar.2012.12.024. Epub Dec. 28, 2012.
Blanchard et al., "Ethoexperimental approaches to the biology of emotion." Annu Rev Psychol. 1988: 39: 43-68. doi: 10.1146/annurev.ps.39.020188.000355.
Bobes, J., "How is recovery from social anxiety disorder defined?" The Journal of Clinical Psychiatry. J Clin Psychiatry. 1998: 59 Suppl 17:12-19.
Brooks et al., "The significance of chirality in drug design and development." Curr Top Med Chem. 2011 ; 11 (7): 760-770. Author Manuscript, published Jan. 12, 2018 (Year: 2018).
Brøsen, K., et al., "Extensive Metabolizers of Debrisoquine Become Poor Metabolizers during Quinidine Treatment." Pharmacol Toxicol. Apr. 1987; 60(4): 312-4. doi: 10.1111/j.1600-0773.1987.tb01758.x.
Carbonaro, T. et al., "Double-blind comparison of the two hallucinogens psilocybin and dextromethorphan: similarities and differences in subjective experiences." Psychopharmacology (Berl). Feb. 2018; 235(2): 521-534. doi: 10.1007/s00213-017-4769-4. Epub Nov. 7, 2017.
Carhart-Harris et al., "Trial of psilocybin versus escitalopram for depression", New England Journal of Medicine (2021); 384(15): 1402-1411. doi: 10.1056/NEJMoa2032994.
Carhart-Harris, "Psilocybin for treatment-resistant depression: fMRI-measured brain mechanisms." Sci Rep. Oct. 13, 2017; 7(1): 13187. doi: 10.1038/s41598-017-13282-7. 11 pages.
Cascorbi, I., "Pharmacogenetics of cytochrome P4502D6: genetic background and clinical implication." Eur J Clin Invest. Nov. 2003: 33 (Suppl 2): 17-22. doi: 10.1046/j.1365-2362.33.s2.3.x.
Chaly and Diksic, "High yield synthesis of 6-[18F]Fluoro-L-dopa by regioselective fluorination of protected L-dopa with [18F]Acetylhypofluorite." J Nucl Med. Dec. 1986; 27(12): 1896-901.
Clinical Trials.gov., ID NCT03537014, "A Multi-site Phase 3 study of MDMA-Assisted Psychotherapy for PTSD (MAPP1)." National Library of Medicine, Sponsor Lykos Therapeutics, ((Aug. 18, 2021) Study Record Version 46) (Year: 2021), 32 pages.
ClinicalTrials.gov ID NCT05277636, "Acute Effects of R- and S-MDMA in Healthy Subjects (R-S-MDMA)." National Library of Medicine, Sponsor University Hospital, Basel, Switzerland, Study start, Oct. 1, 2022, 13 pages.
Cohen, I., et al., "Concomitant drugs associated with increased mortality for MDMA users reported in a drug safety surveillance database." Scientific Reports, (2021) 11: 5997, 9 pages.
Connarn et al., "Pharmacokinetics and Pharmacogenomics of Bupropion in Three Different Formulations with Different Release Kinetics in Healthy Human Volunteers." AAPS J. Sep. 2017; 19(5): 1513-1522. doi: 10.1208/s12248-017-0102-8. Epub Jul. 6, 2017.
Crisp et al., "The antinociceptive effects of 3, 4-methylenedioxymethamphetamine (MDMA) in the rat", Pharmacology Biochemistry and Behavior (1989); 34(3): 497-501. doi: 10.1016/0091-3057(89)90547-9.
Dalgleish, T., et al., "Transdiagnostic Approaches to Mental Health Problems: Current Status and Future Directions." Journal of Consulting and Clinical Psychology, 2020, vol. 88, No. 3, 179-195.
Danforth et al., "Reduction in social anxiety after MDMA-assisted psychotherapy with autistic adults: a randomized, double-blind, placebo-controlled pilot study." Psychopharmacology (2018) 235: 3137-3148 https:/ /doi.org/10.1007 /s00213-018-5010-9. 12 pages.
De La Torre and Farre, "Neurotoxicity of MDMA (ecstasy): the limitations of scaling from animals to humans." Trends Pharmacol Sci. Oct. 2004;25(10):505-8. doi: 10.1016/j.tips.2004.08.001.
De La Torre et al., "MDMA, methamphetamine, and CYP2D6 pharmacogenetics: what is clinically relevant?", Frontiers in Genetics (2012); 3: 235; 8 pages .doi: 10.3389/fgene.2012.00235.
De La Torre et al., "Non-linear pharmacokinetics of MDMA ('ecstasy') in humans." Br J Clin Pharmacol. Feb. 2000; 49(2): 104-9. doi: 10.1046/j.1365-2125.2000.00121.x.
De Vos et al., "Psychedelics and Neuroplasticity: A Systematic Review Unraveling the Biological Underpinnings of Psychedelics." Front Psychiatry. Sep. 10, 2021: 12:724606. doi: 10.3389/fpsyt.2021.724606. eCollection 2021.17 pages.
Doly et al., "Role of Serotonin via 5-HT2B Receptors in the Reinforcing Effects of MDMA in Mice." PLoS One. Nov. 23, 2009; 4(11): e7952. doi: 10.1371/journal.pone.0007952. 10 pages.
Duman et al., "Synaptic plasticity and depression: new insights from stress and rapid-acting antidepressants." Nat Med. Mar. 2016; 22(3): 238-49. doi: 10.1038/nm.4050.
Ellinwood Jr. et al., "Fundamental mechanisms underlying altered behavior following chronic administration of psychomotor stimulants." Biological Psychiatry, Oct. 1, 1980, 15(5):749-757.
Erowid, "Like a Happy Smiley Speed MOMA, Escitalopram & Divalproex." May 29, 2021, Erowid.org Retrieved May 29, 2021. URL: https://www.erowid.org/experiences/exp.php?ID=89532. 6 pages.
Erowid, "Unexpectedly Hard Tripping . . . All Good, Too." Jul. 7, 2021, Erowid, Retrieved Jul. 7, 2021. URL:https://www.erowid.org/experiences/exp.php?ID=108919. 3 pages.
Eurofins SafetyScreen87 Panel, Panlabs, available online at https://www.eurofinsdiscovery.com/catalog/safetyscreen87-panel-tw/PP223, date unknown, document copyright date 2023, 4 pages.
Fantegrossi et al., "Serotonin synthesis inhibition reveals distinct mechanisms of action for MDMA and its enantiomers in the mouse", Psychopharmacology (2005); 181(3): 529-536. doi: 10.1007/s00213-005-0005-8. Epub Oct. 12, 2005.
Fantegrossi et al., "Nantenine: an antagonist of the behavioral and physiological effects of MDMA in mice." Psychopharmacology (2004) 173:270-277.
Feduccia, "MDMA-assisted psychotherapy for PTSD: Are memory reconsolidation and fear extinction underlying mechanisms?" Progress in Neuropsychopharmacology & Biological Psychiatry vol. 84, pp. 221-228, 2019.

(56) References Cited

OTHER PUBLICATIONS

Frith et al., "Toxicity of methylenedioxymethamphetamine (MDMA) in the dog and the rat." Fundam Appl Toxicol. Jul. 1987; 9(1): 110-9. doi: 10.1016/0272-0590(87)90158-8.
Gauvin et al., "Establishing performance characteristics for positive control article selection in drug self-administration studies." Journal of Pharmacological and Toxicological Methods vol. 97, May-Jun. 2019, pp. 13-23.
Glue, P., et al., "Influence of CYP2D6 activity on the pharmacokinetics and pharmacodynamics of a single 20 mg dose of ibogaine in healthy volunteers." J Clin Pharmacol. Jun. 2015;55(6):680-7. doi: 10.1002/jcph.471. Epub Feb. 25, 2015.
Gold and Koob, "MDMA produces stimulant-like conditioned locomotor activity." Psychopharmacology (Berl). 1989; 99(3): 352-6. doi: 10.1007/BF00445556.
Gopisankar, M. G., "CYP2D6 pharmacogenomics." The Egyptian Journal of Medical Human Genetics 18 (2017) 309-313.
Green, R., et al., "MDMA: on the translation from rodent to human dosing." Psychopharmacology (Berl). Jun. 2009; 204(2): 375-8. doi: 10.1007/s00213-008-1453-8. Epub Jan. 13, 2009.
Haberzettl et al., "Animal models of the serotonin syndrome: a systematic review." Behav Brain Res. Nov. 1, 2013: 256: 328-45. doi: 10.1016/j.bbr.2013.08.045. Epub Sep. 1, 2013.
Halberstadt and Geyer, "Characterization of the head-twitch response induced by hallucinogens in mice: detection of the behavior based on the dynamics of head movement," Psychopharmacology (Berl). Jun. 2013;227(4):727-39. doi: 10.1007/s00213-013-3006-z. Epub Feb. 14, 2013.
Halberstadt et al., "Correlation between the potency of hallucinogens in the mouse head-twitch response assay and their behavioral and subjective effects in other species." Neuropharmacology. May 1, 2020: 167: 107933. doi: 10.1016/j.neuropharm.2019.107933. Epub Jan. 7, 2020, 12 pages.
Heydari, A., et al., "Mechanism-based inactivation of CYP2D6 by methylenedioxymethamphetamine." Drug Metab Dispos. Nov. 2004; 32(11): 1213-7. doi: 10.1124/dmd.104.001180. Epub Aug. 24, 2004.
Hilaire et al., "The role of serotonin in respiratory function and dysfunction." Respiratory Physiology & Neurobiology vol. 174, Issues 1-2, Nov. 30, 2010, pp. 76-88.
Holze et al., "Distinct acute effects of LSD, MDMA, and D-amphetamine in healthy subjects", Neuropsychopharmacology (2020); 45(3): 462-471. doi: 10.1038/s41386-019-0569-3. Epub Nov. 16, 2019.
Hysek et al., "Duloxetine inhibits effects of MDMA ("ecstasy") in vitro and in humans in a randomized placebo-controlled laboratory study." PloS One (2012); 7(5): e36476; 15 pages. doi: 10.1371/journal.pone.0036476. Epub May 4, 2012.
Hysek et al., "Effects of the a2-adrenergic agonist clonidine on the pharmacodynamics and pharmacokinetics of 3,4-methylenedioxymethamphetamine in healthy volunteers", The Journal of Pharmacology and Experimental Therapeutics (2012); 340: 286-294. doi: 10.1124/jpet.111.188425. Epub Oct. 27, 2011.
Hysek et al., "MDMA enhances emotional empathy and prosocial behavior." Soc Cogn Affect Neurosci. Nov. 2014; 9(11): 1645-52. doi: 10.1093/scan/nst161. Epub Oct. 4, 2013.
Hysek et al., "Thenorepinephrine transporter inhibitor reboxetine reduces stimulant effects of MOMA ("ecstasy") in humans", Clinical Pharmacology and Therapeutics (2011); 90: 246-255. doi: 10.1038/clpt.2011.78. Epub Jun. 15, 2011.
Inouye et al., "MDMA-assisted therapy for borderline personality disorder." Journal of Psychedelic Studies, 7 (2023) 3, 227-237, DOI:10.1556/2054.2023.00196.
International Preliminary Report on Patentability for International Application No. PCT/IB2023/058939 mailed Mar. 20, 2025, 8 pages.
International Preliminary Report on Patentability for International Application No. PCT/US2022/042353 dated Nov. 7, 2023, 27 pages.
International Preliminary Report on Patentability for International Application No. PCT/US2022/043833 dated Mar. 28, 2024, 5 pages.
International Preliminary Report on Patentability for International Application No. PCT/US2022/045587 dated Apr. 11, 2024, 11 pages.
International Preliminary Report on Patentability for International Application No. PCT/US2022/077432 dated Apr. 11, 2024, 9 pages.
International Search Report and Written Opinion for International Application No. PCT/IB2023/058939 dated Dec. 1, 2023, 11 pages.
International Search Report and Written Opinion for International Application No. PCT/US2023/079137 dated Apr. 29, 2024, 11 pages.
International Search Report and Written Opinion for International Application No. PCT/US2023/086567, dated May 24, 2024, 11 pages.
International Search Report and Written Opinion for International Application No. PCT/US2024/010486 mailed May 17, 2024, 10 pages.
International Search Report and Written Opinion for International Application No. PCT/US2024/032949, mailed Nov. 26, 2024. 11 pages.
International Search Report and Written Opinion for International Application No. PCT/US2024/033081, dated Oct. 24, 2024, 14 pages.
International Search Report and Written Opinion for International Application No. PCT/US2024/036639, mailed Sep. 23, 2024, 11 pages.
International Search Report and Written Opinion for International Application No. PCT/US2024/054056, mailed Feb. 10, 2025, 18 pages.
International Search Report and Written Opinion for International Application No. PCT/US2024/061447, mailed Feb. 26, 2025, 10 pages.
Invitation to Pay Additional Fees for International Application No. PCT/US2023/086567, mailed Mar. 18, 2024. 2 pages.
Invitation to Pay Additional Fees for International Application No. PCT/US2024/010486 mailed Mar. 12, 2024, 2 pages.
Invitation to Pay Additional Fees for International Application No. PCT/US2024/032949, mailed Aug. 6, 2024, 2 pages.
Invitation to Pay Additional Fees for International Application No. PCT/US2024/033081, mailed Aug. 15, 2024, 3 pages.
Jeppesen, U., et al., "Dose-dependent inhibition of CYP1A2, CYP2C19 and CYP2D6 by citalopram, fluoxetine, fluvoxamine and paroxetine." Eur J Clin Pharmacol (1996) 51: 73-78.
Kalant, Harold, "The pharmacology and toxicology of "ecstasy" (MDMA) and related drugs." CMAJ. Oct. 2, 2001; 165(7): 917-28.
Kalivas et al., "MDMA Elicits Behavioral and Neurochemical Sensitization in Rats." Neuropsychopharmacology vol. 18, pp. 469-479 (1998).
Kamilar-Britt and Bedi, "The prosocial effects of 3,4-methylenedioxymethamphetamine (MDMA): Controlled studies in humans and laboratory animals." Neurosci Biobehav Rev. Oct. 2015: 57: 433-46. doi: 10.1016/j.neubiorev.2015.08.016. Epub Sep. 25, 2015.
Kashdan, T. B. & Mcknight, P. E., "The darker side of social anxiety: When aggressive impulsivity prevails over shy inhibition." Current Directions in Psychological Science. Feb. 2010;19(1):47-50.
Kirilly, E, et al., "Acute and long-term effects of a single dose of MDMA on aggression in Dark Agouti rats." Int J Neuropsychopharmacol. Feb. 2006; 9(1): 63-76.
Kiyatkin, "Environmental Conditions Modulate Neurotoxic Effects of Psycho motor Stimulant Drugs of Abuse." Int Rev Neurobiol. 2012 ; 102: 147-171. doi:10.1016/B978-0-12-386986-9.00006-5.
Koenig and Hilber, "The Anti-Addiction Drug Ibogaine and the Heart: A Delicate Relation." Molecules 2015, 20, 2208-2228; doi:10.3390/molecules20022208.
Kolbrich et al., "Physiological and subjective responses to controlled oral 3, 4-methylenedioxymethamphetamine administration", Journal of Clinical Psychopharmacology (2008); 28(4): 432-440. doi:10.1097/JCP.0b013e31817ef470.

(56) References Cited

OTHER PUBLICATIONS

Kotlyar et al., "Inhibition of CYP2D6 Activity by Bupropion." J Clin Psychopharmacol. Jun. 2005; 25(3): 226-9. doi: 10.1097/01.jcp.0000162805.46453.e3.
Lettfuss et al. "Is behavioral sensitization to 3,4-methylenedioxymethamphetamine (MDMA) mediated in part by cholinergic receptors?" Behav Brain Res. May 1, 2013: 244: 116-9. doi: 10.1016/j.bbr.2013.01.033. Epub Feb. 1, 2013.
Lewis et al., "Synthesis of R-and S-MDMA via nucleophilic ring-opening of homochiral N-tosylaziridines", Jul. 12, 2023 (Jul. 12, 2023), Australian Journal of Chemistry, 76(5), pp. 299-310.
Ly et al., "Psychedelics promote structural and functional neural plasticity." Cell Rep. Jun. 12, 2018; 23(11): 3170-3182. doi: 10.1016/j.celrep.2018.05.022.
Lyon et al., "3, 4-Methylenedioxymethamphetamine (MDMA): stereoselective interactions at brain 5-$HT_1$ and 5-$HT_2$ receptors." Psychopharmacology (1986); 88: 525-526. doi: 10.1007/BF00178519.
Madsen et al., "A single psilocybin dose is associated with long-term increased mindfulness, preceded by a proportional change in neocortical 5-HT2A receptor binding." Eur Neuropsychopharmacol. Apr. 2020: 33: 71-80. doi: 10.1016/j.euroneuro.2020.02.001. Epub Mar. 4, 2020.
Mcewen et al., "Stress Effects on Neuronal Structure: Hippocampus, Amygdala, and Prefrontal Cortex." Neuropsychopharmacology. Jan. 2016; 41(1): 3-23. doi: 10.1038/npp.2015.171. Epub Jun. 16, 2015.
Miczek, K., "A new test for aggression in rats without aversive stimulation: Differential effects of d-amphetamine and cocaine." Psychopharmacology (Berl). Feb. 28, 1979; 60(3): 253-9. doi: 10.1007/BF00426664.
Miksys, et al., "Human CYP2D6 and mouse CYP2Ds: organ distribution in a humanized mouse model." Drug Metab Dispos. Oct. 2005; 33(10): 1495-502. doi: 10.1124/dmd.105.005488. Epub Jul. 20, 2005.
Mitchell. "MDMA-assisted therapy for severe PTSD: a randomized, double-blind, placebo-controlled phase 3 study", Nature Medicine (2021); 27(6):1025-1033. doi: 10.1038/s41591-021-01336-3. Epub May 10, 2021.
Mithoefer et al., "The safety and efficacy of {+/−}3,4-methylenedioxymethamphetamine-assisted psychotherapy in subjects with chronic, treatment-resistant posttraumatic stress disorder: the first randomized controlled pilot study." J Psychopharmacol. Apr. 2011; 25(4): 439-52. doi: 10.1177/0269881110378371. Epub Jul. 19, 2010.
Multidisciplinary Association for Psychedelic Studies (MAPS), "A Manual for Adherence Ratings of MDMA-Assisted Therapy for Treatment of Posttraumatic Stress Disorder, Version 6." MAPS, Santa Cruz, CA, Aug. 2021, 52 pages.
Nash et al., "Effect of the R (−) and S (+) isomers of MDA and MDMA on phosphotidyl inositol turnover in cultured cells expressing 5-HT2A or 5-HT2C receptors", Neuroscience Letters (1994); 177(1-2): 111-115. doi: 10.1016/0304-3940(94)90057-4.
National Center for Biotechnology Information, "1-(1,3-benzodioxol-5-yl)-N ,3-dimethylbuta n-2-amine; hydrochloride: PUBCHEM CID 90667266" Pubchem entry (online), pp. 1-9, Mar. 11, 2015; Retrieved on Dec. 2, 2024 from the Internet: [URL: https://pubc hem.ncbi.nlm.nih.gov/compound/90667266].
National Center for Biotechnology Information, "[1-[2-(3,4-Dimethoxyphenyl)ethyl] cycloprop yl] carbamic acid: PUBCHEM CID 150096163" Pubchem entry (online), pp. 1-7, Dec. 13, 2018; Retrieved on Dec. 2, 2024 from the Internet: [URL: https://pubchem.ncbi.nlm.nih.gov/compound/150096163].
National Center for Biotechnology Information, "[1-[(3,4-Dimethoxyphenyl)methyl] cyclobutyl] carbamic acid: PUBCHEM CID 135313815" Pubchem entry (online), pp. 1-8, Dec. 15, 2018; Retrieved on Dec. 2, 2024 from the Internet: [URL: https://pubchem .ncbi.nlm.nih.gov/compound/135313815].
National Center for Biotechnology Information, "[2-(I,3-Benzodioxol-5-yl)-2-methylpropyl] carbamic acid: PUBCHEM CID 115171385" Pubchem entry (online), pp. 1-7, Jan. 29, 2016; Retrieved on Dec. 2, 2024 from the Internet: [URL: https://pubchem.ncbi .nlm.nih.gov/compound/115171385].
National Center for Biotechnology Information "2-(1,3-benzodioxol-5-yl)ethyl carbamothio ic S-acid: PUBCHEM CID 115170245" Pubchem entry (online), pp. 1-7, Jan. 29, 2016; Retrieved on Dec. 1, 2024 from the Internet: [URL: https://pubchem.ncbi.nlm.nih.gov/compound/115170245].
National Center for Biotechnology Information, "Ethyl (2S)-3-(1,3-benzodioxol-5-yl)-2-[(2-methylpropan-2-yl)oxycarbonylamino] propanoate: PUBCHEM CID 57958894" Pubchem entry (online), pp. 1-9, Aug. 19, 2012; Retrieved on Dec. 2, 2024 from the Internet: [URL: https://pubchem.ncbi.nlm.nih.gov/compound/57958894].
National Center for Biotechnology Information, "Ethyl N-[1-chloro-2-(3,4-dimethoxyphenyl) ethyl]carbamate: PUBCHEM CID 89487151" Pubchem entry (online), pp. 1-8, Feb. 13, 2015; Retrieved on Dec. 2, 2024 from the Internet: [URL: https://pubchem.nc bi.nlm.nih.gov/compound/89487151].
National Center for Biotechnology Information, "Ethyl N-[2-(1,3-benzodioxol-5-yl)ethyl] carbamate: PUBCHEM CID 15229637" Pubchem entry (online), pp. 1-9, Feb. 9, 2007; Retrieved on Dec. 1, 2024 from the Internet: [URL: https://pubchem.ncbi.nlm. nih.gov/compound/15229637].
National Center for Biotechnology Information, "Mbdp hydrochloride: PUBCHEM CID 90667265" Pubchem entry (online), pp. 1-10, Mar. 11, 2015; Retrieved on Dec. 2, 2024 from the Internet: [URL: https://pubchem.ncbi.nlm.nih.gov/compound/90667265].
National Center for Biotechnology Information, "Methyl N-[2-(1 ,3-benzodioxol-5-yl) ethyl]carbamodithioate: PUBCHEM CID 44125045" Pubchem entry (online), pp. 1-8, Jul. 27, 2009; Retrieved on Dec. 1, 2024 [URL: https://pubchem.ncbi.nlm.nih.gov/compound/44125045].
National Center for Biotechnology Information, "Methyl N-[(2R)-I-(1,3-benzodioxol-5-yl)-3-chloropropan-2-yl]carbamate: PUBCHEM CID 166107066" Pubchem entry (online), pp. 1-7, Dec. 20, 2022; Retrieved on Dec. 2, 2024 from the Internet: [URL: https:// pubchem.ncbi.nlm.nih.gov/compound/166107066].
National Center for Biotechnology Information, "Methyl N-[I-(I , -benzodioxol-5-yl) propan-2-yl]carbamate: PUBCHEM CID 168188536" Pubchem entry (online), pp. 1-9, May 30, 2023; Retrieved on Dec. 1, 2024 from the Internet: [URL: https://pubchem.ncbi.nlm.nih.gov/compound/168188536].
National Center for Biotechnology Information, 'N-Methyl-1-(3,4-methylenedioxyphenyl)-2-butananiine: PUBCHEM CID 124844 Pubchem entry (online), pp. 1-8, Jul. 19, 2005; Retrieved on Dec. 2, 2024 from the Internet: [URL: https://pubchem.ncbi.nlm.nih.gov/compound/124844].
National Center for Biotechnology Information, 'N-Moc-MDMA: PUBCHEM CID 165361551 Pubchem entry (online), pp. 1-11, Oct. 11, 2022; Retrieved on Dec. 2, 2024 from the Internet: [URL: https://pubchem.ncbi.nlm.nih.gov/compound/165361 551].
National Center for Biotechnology Infonnation, "Methyl N-[(2S)-1-(1,3-benzodioxol-5-yl)-3-chloropropan-2-yl]carbamate: PUBCHEM CID 166107086" Pubchem entry (online), pp. 1-7, Dec. 20, 2022; Retrieved on Dec. 2, 2024 from the Internet: [URL: https:// pubchem.ncbi.nlm.nih.gov/compound/166107086].
National Center for Biotechnology Information, "Methyl N-[4-(3,4-dimethoxyphenyl) oxan-4-yl]carbamate: PUBCHEM CID 142770320" Pubchem entry (online), pp. 1-8, Dec. 7, 2019; Retrieved on Dec. 2, 2024 from the Internet: [URL: https://pubchem.ncbi.nlm.nih.gov/compound/142770320].
Navarro and Maldonado, "Behavioral profile of 3,4-methylenedioxy-methamphetamine (MDMA) in agonistic encounters between male mice." Prog Neuropsychopharmacol Biol Psychiatry. Feb. 1999; 23(2): 327-34. doi: 10.1016/s0278-5846(98)00100-6.
Navarro and Maldonado, "Effects of acute, subchronic and intermittent MDMA ('Ecstasy') administration on agonistic interactions between male mice." Aggressive Behavior (2004) vol. 30, Issue 1, p. 84-91.
Nelson and Chiavegatto, "Molecular basis of aggression." Trends Neurosci. Dec. 2001; 24(12): 713-9. doi: 10.1016/s0166-2236(00)01996-2.

(56) References Cited

OTHER PUBLICATIONS

Neumann et al., "Aggression and anxiety: social context and neurobiological links, Front Behav Neurosci." Mar. 30, 2010: 4: 12. doi: 10.3389/fnbeh.2010.00012. eCollection 2010, 16 pages.
O'Mathuna, B., et al., "The Consequences of 3,4-Methylenedioxymethamphetamine Induced CYP2D6 Inhibition in Humans." J Clin Psychopharmacol. Oct. 2008; 28(5): 523-9. doi: 10.1097/JCP.0b013e318184ff6e.
Parrot, A C, "Is ecstasy MDMA? A review of the proportion of ecstasy tablets containing MDMA, their dosage levels, and the changing perceptions of purity." Psychopharmacology (Berl). May 2004; 173(3-4): 234-41. doi: 10.1007/s00213-003-1712-7. Epub Mar. 9, 2004.
Parrott AC, "Human psychopharmacology of Ecstasy (MDMA): a review of 15 years of empirical research." Hum Psychopharmacol. Dec. 2001; 16(8): 557-577.
Peters. "Drug testing in blood: validated negative-ion chemical ionization gas chromatographic-mass spectrometric assay for enantioselective measurement of the designer drugs MDEA, MDMA, and MDA and its application to samples from a controlled study with MDMA", Clinical Chemistry (2005); 48(9); 1811-1822. doi: 10.1373/clinchem.2005.052746. Epub Aug. 11, 2005.
Pitts et al., "3, 4-Methylenedioxymethamphetamine increases affiliative behaviors in squirrel monkeys in a serotonin 2A receptor-dependent manner", Neuropsychopharmacology (2017); 42(10): 1962-1971. doi: 10.1038/npp.2017.80. Epub Apr. 20, 2017.
Pizzaro et al., "Determination of MDMA and its Metabolites in Blood and Urine by Gas Chromatography—Mass Spectrometry and Analysis of Enantiomers by Capillary Electrophoresis." J Anal Toxicol. Apr. 2002; 26(3): 157-65. doi: 10.1093/jat/26.3.157.
Pokorny et al., "Effect of Psilocybin on Empathy and Moral Decision-Making." International Journal of Neuropsychopharmacology (2017) 20(9): 747-757.
Pubchem SID 297429685 deposited on Jan. 27 (Jan. 27, 2016) p. 1-5. 2, structure.
Pubchem SID 459067002 deposited on Dec. 20, 2021 (Dec. 20, 2021) p. 1-5.
Saez-Briones and Hernandez, "MDMA (3,4-Methylenedioxymethamphetamine) Analogues as Tools to Characterize MDMA-Like Effects: An Approach to Understand Entactogen Pharmacology." Curr Neuropharmacol. Sep. 2013; 11(5): 521-34. doi: 10.2174/1570159X11311050007.
Sager et al., "In vitro to in vivo extrapolation of the complex drug-drug interaction of bupropion and its metabolites with CYP2D6; simultaneous reversible inhibition and CYP2D6 downregulation." Biochem Pharmacol. Jan. 1, 2017: 123: 85-96. doi: 10.1016/j.bcp.2016.11.007. Epub Nov. 9, 2016.
Sandtner et al., "Binding Mode Selection Determines the Action of Ecstasy Homologs at Monoamine Transporters." Mol Pharmacol. Jan. 2016; 89(1): 165-75. doi:10.1124/mol.115.101394. Epub Oct. 30, 2015.
Schenk and Bradbury, "Persistent sensitisation to the locomotor activating effects of MDMA following MDMA self-administration in rats." Pharmacol Biochem Behav. May 2015: 132: 103-107. doi: 10.1016/j.pbb.2015.03.001. Epub Mar. 8, 2015.
Schmid et al., "Acute subjective effects in LSD-and MDMA-assisted psychotherapy", Journal of Psychopharmacology (2021); 35(4): 362-374. doi: 10.1177/0269881120959604. Epub Oct. 8, 2020.
Segura, M., et al., "Contribution of cytochrome P450 2D6 to 3,4-methylenedioxymethamphetamine disposition in humans: use of paroxetine as a metabolic inhibitor probe." Clin Pharmacokinet. 2005; 44(6): 649-60. doi: 10.2165/00003088-200544060-00006.
Simmler. "Pharmacological characterization of designer cathinones in vitro", British Journal of Pharmacology (2013) 168(2): 458-470. doi: 10.1111/j.1476-5381.2012.02145.x.
Spanos and Yamamoto, "Acute and subchronic effects of methylenedioxymethamphetamine [(+/−)MDMA] on locomotion and serotonin syndrome behavior in the rat." Pharmacol Biochem Behav. Apr. 1989; 32(4): 835-40. doi: 10.1016/0091-3057(89)90044-0.
Steuer et al., "Impact of cytochrome P450 2D6 function on the chiral blood plasma pharmacokinetics of 3, 4-methylenedioxymethamphetamine (MDMA) and its phase I and II metabolites in humans", PloS One (2016); 11(3): e0150955; 19 pages. doi: 10.1371/journal.pone.0150955.
Straumann, et al., "Acute effects of R-MDMA, S-MDMA, and racemic MDMA in a randomized double-blind cross-over trial in healthy participants." Neuropsychopharmacology. Dec. 2024; 50(2): 362-371. doi: 10.1038/s41386-024-01972-6. Epub Aug. 23, 2024.
Thomas et al., "Psilocybin and Ketamine Acutely Promote Wakefulness, Suppress REM Sleep but Differentially Modulate High Frequency EEG Oscillatory Power in Wistar Kyoto Rats—a Preliminary Analysis." ACNP 59th Annual Meeting: Poster Session I, Neuropsychopharmacology. Dec. 2020;45(Suppl 1):68-169. M140, doi: 10.1038/s41386-020-00890-7, 1 page.
Torner, "Actions of Prolactin in the Brain: From Physiological Adaptations to Stress and Neurogenesis to Psychopathology." Front Endocrinol (Lausanne). Mar. 30, 2016: 7: 25. doi: 10.3389/fendo.2016.00025. eCollection 2016. 6 pages.
Traynor, J.M., et al., "MDMA-Assisted Psychotherapy for Borderline Personality Disorder." Focus, 2022, 20(4):358-67, (focus.psychiatryonline.org).
U.S. Appl. No. 18/934,442, filed Nov. 1, 2024, by Khan et al.
U.S. Appl. No. 18/990,840, filed Dec. 20, 2024, by Rao et al.
Willins and Meltzer, "Direct injection of 5-HT2A receptor agonists into the medial prefrontal cortex produces a head-twitch response in rats." J Pharmacol Exp Ther. Aug. 1997; 282(2): 699-706.
Young, M.B., et al., "3,4-Methylenedioxymethamphetamine facilitates fear extinction learning." Transl Psychiatry. Sep. 15, 2015; 5(9): e634. 8 pages.
Yubero-Lahoz et al., "Changes in CYP1A2 Activity in Humans after 3,4-Methylenedioxymethamphetamine (MDMA, Ecstasy) Administration Using Caffeine as a Probe Drug." Drug Metab. Pharmacokinet. 27 (6): 605-613 (2012).
Zapata-Torres et al., "Quantum-chemical, NMR and X-ray diffraction studies on (±)-1-[3, 4-(methylenedioxy) phenyl]-2-methylaminopropane", Journal of Molecular Graphics and Modelling (2008); 26(8): 1296-1305.
Alexander, J., et al., "(Acyloxy)alkyl carbamates as novel bioreversible prodrugs for amines: increased permeation through biological membranes." J Med Chem. Feb. 1988;31(2):318-22. doi: 10.1021/jm00397a008.
Buttonwood, "Single crystal x-ray diffraction experiment backwards: from CIF to genuine set of raw data without performing actual experiment." Chemistry Stack Exchange, Jun. 28, 2017, URL:https://chemistry.stackexchange.com/questions/76950/singlecrystal-x-ray-diffraction-experiment-backwards-from-cif-to-genuine-set?, retrieved Jul. 22, 2025, 6 pages.
Cambridge Crystallographic Data Centre, CSD Entry: BEQRUN, Deposited Feb. 23, 2018, retrieved Jul. 22, 2025, https://www.ccdc.cam.ac.uk/structures/Search?Ccdcid=BEQRUN&DatabasToSearch=Published, 3 pages.
Extended European Search Report for European Application No. 22865560.1 mailed Jul. 28, 2025, 6 pages.
Extended European Search Report for European Application No. 22877644.9 mailed Jul. 11, 2025, 8 pages.
International Preliminary Report on Patentability for International Application No. PCT/US2023/079137 mailed May 22, 2025, 9 pages.
International Preliminary Report on Patentability for International Application No. PCT/US2024/010486 mailed Jul. 17, 2025, 7 pages.
Partial Supplementary European Search Report for European Application No. 22877438.6 mailed Jul. 7, 2025, 16 pages.
Shulgin, A. T., "The Background and Chemistry of MDMA." J Psychoactive Drugs. Oct.-Dec. 1986;18(4):291-304. doi: 10.1080/02791072.1986.10472361.
U.S. Appl. No. 19/145,450, filed Jul. 2, 2025, by Gibbs et al.
Australian and New Zealand Clinical Trials Registry, Identifier ACTRN12622001335785. "A Phase 1 Randomized, First-in-

(56) References Cited

OTHER PUBLICATIONS

Human, Double-Blind, Placebo-Controlled Study to Evaluate the Safety, Tolerability, Pharmacokinetics, and Pharmacodynamics of Single-Ascending Doses of EMP-01 in Healthy Adult Volunteers." [Internet], Sydney (NSW): NHMRC Clinical Trials Centre, University of Sydney Australia; (Oct. 18, 2022), last updated Feb. 14, 2024 [retrieved from the Internet Oct. 23, 2025, from https://www.anzctr.org.au/Trial/Registration/TrialReview.aspx?id=384394&isReview=true]; 7 pages.

EP Application No. 22877438.6, Extended European Search Report mailed Sep. 30, 2025; Applicant EmpathBio, Inc.; 8 pages.

Ozber N., et al., "Bioproduction of 3,4-methylenedioxymethamphetamine and derivatives." BioDesign Research, Jun. 2025, vol. 7, Issue 2, 100011, 11 pages.

U.S. Appl. No. 19/366,168, filed Oct. 22, 2025; Inventor Fawaz, Majed et al.

U.S. Appl. No. 19/345,242, filed Sep. 30, 2025; Inventor Perni et al.

EP Application No. 22870763.4, Extended European Search Report mailed Nov. 13, 2025; ATAI Life Sciences AG; 8 pages.

EP Application No. 22917528.6, Extended European Search Report mailed Nov. 24, 2025; Applicant EmpathBio, Inc; 8 pages.

PCT Application No. PCT/US2024/033081, International Preliminary Report on Patentability mailed Dec. 18, 2025; Applicant Empathbio, Inc.; 9 pages.

PCT Application No. PCT/US2024/036639, International Preliminary Report on Patentability mailed Jan. 15, 2026, Applicant Empathbio, Inc.; 8 pages.

Plotka et al., "Common methods for the chiral determination of amphetamine and related compounds I. Gas, liquid and thin-layer chromatography," TrAC Trends in Analytical Chemistry, (Jul. 2011), 30(7): 1139-1158, DOI:10.1016/j.trac.2011.03.013.

U.S. Appl. No. 19/431,012, filed Dec. 23, 2025; Inventor Fawaz, Majed et al.

* cited by examiner

PREPARATION OF OPTICALLY ACTIVE ENANTIOMERS OF PIPERONYL AMINES BY RESOLUTION OF THE DIASTEREOMERIC SALTS

CROSS-REFERENCE TO RELATED APPLICATION

The present application claims the benefit of priority to U.S. Provisional Application No. 63/245,496, filed Sep. 17, 2021, the contents of which are hereby incorporated by reference in its entirety.

BACKGROUND 3,4-methylenedioxymethamphetamine (MDMA) is considered the prototype of a class of compounds called entactogens, which means "to touch within", their main characteristic being their ability to increase feelings of love, empathy and closeness towards others. Structurally, MDMA is a ring-substituted phenethylamine with a chiral molecular center that gives rise to two stereoisomers: S-(+)-MDMA and R-(−)-MDMA. Typically, effects of the former resemble those of psychostimulants and are primarily mediated by dopaminergic and noradrenergic pathways, including increases in motor activity and euphoria, whereas the latter induces qualitative effects similar to classical psychedelics, such as ego-dissolution and perceptive alterations, mediated by serotonergic pathways, including direct 5-HT2A receptor agonism. The molecular mechanisms for these differences are supported by preclinical evidence and point to a higher therapeutic index for the R-enantiomer.

There remains a need for improved processes of making enantiomers of 3,4-methylenedioxymethamphetamine and analogs thereof.

SUMMARY

In an aspect, the present disclosure provides a process for resolving enantiomers of piperonyl amines.

In some embodiments, the present disclosure provides a process for resolving the (R) or (S) enantiomers of 3,4-methylenedioxymethamphetamine (MDMA).

In embodiments, provided herein is a process for resolving the (S)- and (R)-enantiomers of a compound of Formula (I):

(I)

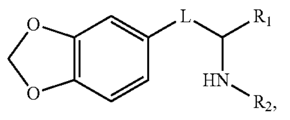

wherein L is a $C_1$-$C_5$ alkylene, carbocyclyl, or heterocyclyl;

$R^1$ is selected from the group consisting of alkyl, benzyl and phenethyl; and $R^2$ is selected from the group consisting of hydrogen, alkyl, benzyl and phenethyl;

the process comprising:

(a) mixing a compound of Formula (I) and a chiral acid in a solvent to provide a diastereomeric salt of Compound (I) and (b) resolving the (S)- and (R)-enantiomers of the compound of Formula (I), wherein the enantiomeric excess of the compound of Formula (I) is less than about 50%.

In embodiments, the resolution (b) comprises preferential crystallization of the (S)- or (R)-enantiomer of the compound of Formula (I).

In embodiments, the chiral acid is selected from the group consisting of(S)-2-methoxy-2-phenylacetic acid, L-tartaric acid, dibenzoyl-L-tartaric acid, di-p-toluoyl-L-tartaric acid, L-ascorbic acid, L-aspartic acid, (S)-(+)-mandelic acid, (−)-di-O-isopropyledene-2-keto-L-gulonic acid and (1R, 3S)-(+)-camphoric acid, In embodiments, the chiral acid is selected from the group consisting of (R)-2-methoxy-2-phenylacetic acid, D-tartaric acid, dibenzoyl-D-tartaric acid, di-p-toluoyl-D-tartaric acid, D-ascorbic acid, D-aspartic acid, (R)-(−)-mandelic acid, and (1S, 3R)-(−)-camphoric acid.

In embodiments, the chiral acid is (S)-2-methoxy-2-phenylacetic acid.

DETAILED DESCRIPTION

Throughout this disclosure, various patents, patent applications and publications are referenced. The disclosures of these patents, patent applications and publications in their entireties are incorporated into this disclosure by reference for all purposes to describe the state of the art more fully as known to those skilled therein as of the date of this disclosure. This disclosure will govern in the instance that there is any inconsistency between the patents, patent applications and publications cited and this disclosure.

Definitions

For convenience, certain terms employed in the specification, examples and claims are collected here. Unless defined otherwise, all technical and scientific terms used in this disclosure have the same meanings as commonly understood by a person skilled in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example, in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The term "pharmaceutically acceptable salts" includes both acid addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, amino acids (such as glycine, alanine, arginine, -asparagine, aspartic acid, cysteine, glutamine, glutamic acid, histidine, isoleucine, leucine, lysine, methionine, phenylalanine, proline, serine, threonine, tryptophan, tyrosine, value), etc. The acids that may be used to prepare pharmaceutically acceptable acid addition salts of such basic compounds are those that form non-toxic acid addition salts, i.e., salts containing pharmaceutically acceptable anions, including but not limited to malate, oxalate, chloride, bromide, iodide, nitrate, acetate, tartrate, oleate, fumarate, formate, benzoate, glutamate, methanesulfonate, benzenesulfonate, and p-toluenesulfonate salts. Those skilled in the art will further recognize that acid addition salts may be prepared by reaction of the compounds with the appropriate inorganic or organic acid via any of a number of known methods.

When a range of values is listed, it is intended to encompass each value and sub-range within the range. For example, "C1-C6 alkyl" is intended to encompass C1, C2, C3, C4, C5, C6; C1-6, C1-5, C1-4, C1-3, C1-2, C2-6, C2-5, C2-4, C2-3, C3-6, C3-5, C3-4, C4-6, C4-5, and C5-6 alkyl.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight, or branched divalent hydrocarbon chain radical, and having from one to twelve carbon atoms. Non-limiting examples of $C_1$-$C_{12}$ alkylene include methylene, ethylene, propylene, n-butylene, and the like. The alkylene chain is attached to the rest of the molecule through a single bond and to a radical group (e.g., those described herein) through a single bond. The points of attachment of the alkylene chain to the rest of the molecule and to the radical group can be through one carbon or any two carbons within the chain. Unless stated otherwise specifically in the specification, an alkylene chain can be optionally substituted.

"Carbocyclyl," "carbocyclic ring" or "carbocycle" refers to a rings structure, wherein the atoms which form the ring are each carbon, and which is attached to the rest of the molecule by a single bond. Carbocyclic rings can comprise from 3 to 20 carbon atoms in the ring. Carbocyclic rings include e.g., aryls and cycloalkyl as defined herein. Unless stated otherwise specifically in the specification, a carbocyclyl group can be optionally substituted.

"Aryl" refers to a hydrocarbon ring system comprising hydrogen, 6 to 18 carbon atoms and at least one aromatic ring, and which is attached to the rest of the molecule by a single bond. For purposes of this disclosure, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the "aryl" can be optionally substituted.

"Cycloalkyl" refers to a stable non-aromatic monocyclic or polycyclic fully saturated hydrocarbon consisting solely of carbon and hydrogen atoms, which can include fused, bridged, or spirocyclic ring systems, having from three to twenty carbon atoms (e.g., having from three to ten carbon atoms) and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethylbicyclo[2.2.1]heptanyl, and the like. Unless otherwise stated specifically in the specification, a cycloalkyl group can be optionally substituted.

"Heterocyclyl," "heterocyclic ring" or "heterocycle" refers to a stable saturated, unsaturated, or aromatic 3- to 20-membered ring which consists of two to nineteen carbon atoms and from one to six heteroatoms selected from the group consisting of nitrogen, oxygen and sulfur, and which is attached to the rest of the molecule by a single bond. Heterocyclyl or heterocyclic rings include heteroaryls, heterocyclylalkyls, heterocyclylalkenyls, and hetercyclylalkynyls. Unless stated otherwise specifically in the specification, the heterocyclyl can be a monocyclic, bicyclic, tricyclic or tetracyclic ring system, which can include fused, bridged, or spirocyclic ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

The term "substituted" used herein means any of the groups described herein (e.g., alkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $—NR_gR_h$, $—NR_gC(═O)R_h$, $—NR_gC(═O)NR_gR_h$, $—NR_gC(═O)ORh$, $—NR_gSO_2R_h$, $—OC(═O)$ $NR_gR_h$, $—OR_g$, $—SR_g$, $—SOR_g$, $—SO_2R_g$, $—OSO_2R_g$, $—SO_2OR_g$, $=NSO_2R_g$, and $—SO_2NR_gR_h$. "Substituted" also means any of the above groups in which one or more hydrogen atoms are replaced with $—C(=O)R_g$, $—C(=O)OR_g$, $—C(=O)NR_gR_h$, $—CH_2SO_2R_g$, $—CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

Methods

While the racemate is the most commonly administered form of MDMA currently, recent research suggests that there are distinct differences in the pharmacology of the two enantiomers. Hence, the development of efficient asymmetric strategies for producing enantiopure MDMA and other piperonyl amines is of high importance.

Enantiomers of MDMA have been separated via the use of removable chiral auxiliaries, however the use of chiral auxiliaries necessitates multiple chemical steps to install, utilize, and cleave the auxiliary which is required in stoichiometric quantities resulting in poor step- and atom-economy. Lourenco et al, *J Pharmaceutical and Biomedical Analysis,* 2013, 73, 13-17 were able to separate enantiomers of MDMA by batch chromatography with peak shaving and recycling. However, there are multiple disadvantages associated with chromatography, such as requirement for repetitive extractions, large volumes of organic-based mobile phase for component elution, and the generation of significant solvent waste and disposal costs.

This present disclosure describes methods for the preparation of optically active enantiomers of compounds of Formula (I):

(I)

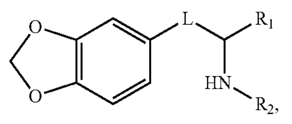

wherein L, $R_1$, and $R_2$ are defined herein, by resolution of its diastereomeric salts.

Using the methods disclosed herein enantiomers of compounds of Formula (I), such as MDMA can be obtained in high enantiomeric purity. The present methods offer advantages over prior routes, where the resolution of racemic MDMA via selective crystallization of diastereomeric salt proved to be an ineffective method for synthesizing MDMA in high enantiomeric excess (see e.g., Dunlap et al, *ACS Chem Neuroscience,* 2018, 9 (10), 2408-2427, and Pizarro et al, *Bioorganic and Medicinal Chemistry,* 2002, 10, 1085-1092). The methods disclosed herein are also superior to both the chromatography and the chiral auxiliary methods for the ease of operation, the cost effectiveness, and the ability to recycle the chiral resolving acid, and utilize racemic MDMA which is readily available.

In embodiments, optically active enantiomers of compounds disclosed herein, e.g., compounds of Formula (I) display an improved pharmacological profile compared to the corresponding racemic mixtures. In embodiments, the resolution methods described herein are performed by combining a racemic mixture of enantiomers of the amine and a resolving acid with a defined stereospecificity in a solvent to form a solution and said resolving acid is capable of binding with at least one of the enantiomers to form a crystalline precipitate. This single diastereomeric solid can then be freebased by treating with a base to provide the optically active enantiomer. In embodiments, if the other enantiomer is desired, then the filtrate can be concentrated to a residue and the resulting opposite diastereomer is freebased as previously to provide the desired compound.

The present disclosure provides a process for resolving the (S)- and (R)-enantiomers of a compound of Formula (I):

(I)

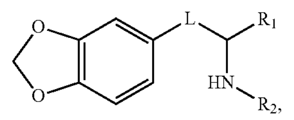

wherein L is a $C_1$-$C_5$ alkylene, carbocyclyl, or heterocyclyl;

$R^1$ is selected from the group consisting of alkyl, benzyl and phenethyl; and $R^2$ is selected from the group consisting of hydrogen, alkyl, benzyl and phenethyl;

the process comprising:

(a) mixing a compound of Formula (I) and a chiral acid in a solvent to provide a diastereomeric salt of Compound (I) and (b) resolving the (S)- and (R)-enantiomers of the compound of Formula (I), wherein the enantiomeric excess of the compound of Formula (I) is less than about 50%.

In some embodiments of the compounds of Formula (I), $R^1$ is selected from the group consisting of alkyl, benzyl and phenethyl.

In some embodiments of the compounds of Formula (I), $R^1$ is alkyl.

In some embodiments of the compounds of Formula (I), $R^1$ is benzyl.

In some embodiments of the compounds of Formula (I), $R^1$ is phenethyl.

In some embodiments of the compounds of Formula (I), $R^2$ is selected from the group consisting of hydrogen, alkyl, benzyl and phenethyl.

In some embodiments of the compounds of Formula (I), $R^2$ is hydrogen.

In some embodiments of the compounds of Formula (I), $R^2$ is alkyl.

In some embodiments of the compounds of Formula (I), $R^2$ is benzyl.

In some embodiments of the compounds of Formula (I), $R^2$ is phenethyl.

In some embodiments of the compounds of Formula (I), $R^1$ and $R^2$ are independently $C_1$-6 alkyl.

In some embodiments of the compounds of Formula (I), $R^1$ and $R^2$ are independently $C_1$-3 alkyl.

In some embodiments of the compounds of Formula (I), $R^1$ and $R^2$ are methyl.

In some embodiments of the compounds of Formula (I), $R^1$ is $C_{1-6}$ alkyl and $R^2$ is hydrogen.

In some embodiments of the compounds of Formula (I), $R^1$ is $C_{1-3}$ alkyl and $R^2$ is hydrogen.

In some embodiments of the compounds of Formula (I), $R^1$ is methyl and $R^2$ is hydrogen.

In some embodiments of the compounds of Formula (I), L is methylene.

In some embodiments of the compounds of Formula (I), L is $C_{1-6}$ alkylene.

In some embodiments of the compounds of Formula (I), L is $C_{1-3}$ alkylene.

In some embodiments of the compounds of Formula (I), L is $—(CH_2)_k—$, wherein k is 1, 2, or 3.

In some embodiments of the compounds of Formula (I), L is $—CH_2—$.

In some embodiments of the compounds of Formula (I), $R^1$ and $R^2$ are methyl and L is methylene.

In some embodiments of the compounds of Formula (I), $R^1$ is methyl and $R^2$ is hydrogen and L is methylene.

In some embodiments, the solvent is selected from the group consisting of toluene, acetonitrile, methanol, ethanol, isopropanol, dichloromethane, and mixtures thereof.

In some embodiments, the solvent is an aromatic solvent e.g., toluene.

In some embodiments, the solvent is an alcohol e.g., methanol, ethanol or isopropanol.

In some embodiments, the solvent is a chlorinated solvent e.g., dichloromethane, dichloroethane and the like.

In some embodiments, the solvent is an ether solvent such as., tetrahydrofuran, dioxane, diethyl ether.

In some embodiments, the solvent is ethyl acetate.

In some embodiments, the solvent is acetonitrile.

In some embodiments, step (a) comprises mixing a compound of Formula (I) and a chiral acid in a solvent while maintaining the temperature at about 20 to 25° C.

In some embodiments, the solution of a compound of Formula (I) and the chiral acid is mixed for about 0.5-48 hours, including about 0.5 hours, about 1 hours, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, to about 48 hours or more, including all subranges and values therebetween.

In some embodiments, the mixture of step (a) further comprises an anti-solvent. In some embodiments, the anti-solvent is a hydrocarbon solvent or an ether solvent.

In some embodiments, the anti-solvent is selected from the group consisting of heptanes and methyl t-butyl ether.

In some embodiments, the anti-solvent is hexane, pentane, or heptane.

In some embodiments, the Step (a) mixture comprises about 0.5 molar equivalents of the chiral acid relative to amount of racemate.

In some embodiments the Step (a) mixture comprises about 1.0 molar equivalents of the chiral acid relative to amount of racemate.

In some embodiments, the chiral acid is selected from the group consisting of(S)-2-methoxy-2-phenylacetic acid, L-tartaric acid, dibenzoyl-L-tartaric acid, di-p-toluoyl-L-tartaric acid, L-ascorbic acid, L-aspartic acid, (S)-(+)-mandelic acid, (−)-di-O-isopropyledene-2-keto-L-gulonic acid and (1R, 3S)-(+)-camphoric acid. In some embodiments, the chiral acid is (S)-2-methoxy-2-phenylacetic acid.

In some embodiments, the chiral acid is (S)-2-methoxy-2-phenylacetic acid, L-tartaric acid, or dibenzoyl-L-tartaric acid.

In some embodiments, the chiral acid is (S)-2-methoxy-2-phenylacetic acid. In embodiments, the chiral acid is L-tartaric acid.

In embodiments, the chiral acid is dibenzoyl-L-tartaric acid.

In embodiments, the chiral acid is di-p-toluoyl-L-tartaric acid.

In embodiments, the chiral acid is L-ascorbic acid.

In embodiments, the chiral acid is L-aspartic acid.

In embodiments, the chiral acid is (S)-(+)-mandelic acid.

In embodiments, the chiral acid is (−)-di-O-isopropyledene-2-keto-L-gulonic acid.

In embodiments, the chiral acid is and (1R, 3S)-(+)-camphoric acid.

In some embodiments, the chiral acid is selected from the group consisting of (R)-2-methoxy-2-phenylacetic acid, D-tartaric acid, dibenzoyl-D-tartaric acid, di-p-toluoyl-D-tartaric acid, D-ascorbic acid, D-aspartic acid, (R)-(−)-mandelic acid, (+)-di-O-isopropyledene-2-keto-D-gulonic acid and (1S, 3R)-(−)-camphoric acid. In some embodiments, the chiral acid is (R)-2-methoxy-2-phenylacetic acid.

In some embodiments, the chiral acid is (R)-2-methoxy-2-phenylacetic acid.

In embodiments, the chiral acid is D-tartaric acid.

In embodiments, the chiral acid is dibenzoyl-D-tartaric acid.

In embodiments, the chiral acid is di-p-toluoyl-D-tartaric acid.

In embodiments, the chiral acid is D-ascorbic acid.

In embodiments, the chiral acid is D-aspartic acid.

In embodiments, the chiral acid is (R)-(−)-mandelic acid.

In embodiments, the chiral acid is (+)-di-O-isopropyledene-2-keto-D-gulonic acid.

In embodiments, the chiral acid is and (1S, 3R)-(−)-camphoric acid.

In some embodiments, the chiral acid is (R)-2-methoxy-2-phenylacetic acid, D-tartaric acid, or dibenzoyl-D-tartaric acid.

In some embodiments of the methods disclosed herein, the diastereomeric chiral salt precipitate comprises the (R)-enantiomer of the compound of Formula (I).

In some embodiments of the methods disclosed herein, the diastereomeric chiral salt precipitate comprises the (S)-enantiomer of the compound of Formula (I).

In some embodiments of the methods of resolving a compound of Formula (I), the method further comprises isolating the preferentially crystallized diastereomeric salt of the compound of Formula (I). In some embodiments, the diastereomeric salt is isolated by filtration.

In some embodiments, after resolving the compound of Formula (I), the other enantiomer (i.e. the enantiomer which does not form a chiral salt with the resolving agent) can be recovered from the mother liquor derived from the resolution step.

In some embodiments of the methods disclosed herein, mixing a compound of Formula (I) and a chiral acid in a solvent provides diastereomeric salt precipitate of Formula (I-a):

(I-a)

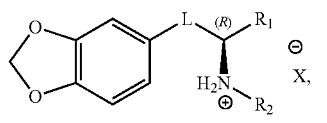

wherein X is the conjugate base of a chiral acid, e.g., as described herein. In some embodiments, the diastereomeric salt precipitate of Formula (I-a) is isolated by filtration and the mother liquor concentrated to give a compound of Formula (1-b).

In some embodiments of the methods disclosed herein, mixing a compound of Formula (I) and a chiral acid in a solvent provides diastereomeric salt precipitate of formula:

(I-b)

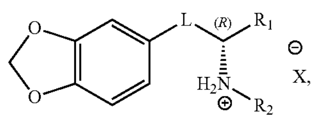

wherein X is the conjugate base of a chiral acid, e.g., as described herein. In some embodiments, the diastereomeric salt precipitate of Formula (I-b) is isolated by filtration and the mother liquor concentrated to give a compound of Formula (1-a).

In some embodiments of the methods disclosed herein, mixing a compound of Formula (I) and a chiral acid in a solvent provides diastereomeric salt precipitate of formula:

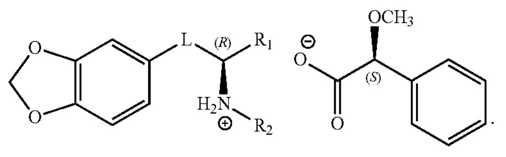

In some embodiments of the methods disclosed herein, mixing a compound of Formula (I) and a chiral acid in a solvent provides diastereomeric salt precipitate of formula:

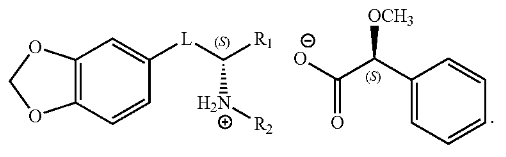

In some embodiments of the methods of resolving a compound of Formula (I), the method further comprises combining the crystallized diastereomeric salt and a base to provide enantioenriched free base of the (S)- or (R)-enantiomer of the compound of Formula (I).

In some embodiments, the base is selected from the group consisting of hydroxides, alkoxides (e.g., methoxide, ethoxide), alkali metal amides (e.g., lithium diisopropylamide), hydrides (e.g., NaH), organolithium, or Grignard reagents. For bases that require a counterion, exemplary counterions include alkali metals, alkaline earth metals, e.g., $Li^+$, $Na^+$, $K^+$, $Ca^{2+}$, $Mg^{2+}$, or organic counterions like a tetra-alkyl ammonium. In some embodiments, the base is a hydroxide base. In some embodiments, the base is sodium hydroxide.

In some embodiments, the resolution (b) comprises preferential crystallization of the (S)- or (R)-enantiomer of the compound of Formula (I).

In some embodiments, the diastereomeric salt comprising the (S)-enantiomer of the compound of Formula (I) is preferentially crystallized.

In some embodiments, the diastereomeric salt comprising the (R)-enantiomer of the compound of Formula (I) is preferentially crystallized.

In some embodiments, the compound of Formula (I) has an enantiomeric excess ("ee") of less than about 50% ee before the compound of Formula (I) is resolved by the methods disclosed herein, less than about 45% before the compound of Formula (I) is resolved, less than about 40% before the compound of Formula (I) is resolved, less than about 35% before the compound of Formula (I) is resolved, less than about 30% before the compound of Formula (I) is resolved, less than about 30% before the compound of Formula (I) is resolved, less than about 25% before the compound of Formula (I) is resolved, less than about 20% before the compound of Formula (I) is resolved, less than about 15% before the compound of Formula (I) is resolved, less than about 10% before the compound of Formula (I) is resolved, less than about 5% before the compound of Formula (I) is resolved, including all subranges and values therebetween. In some embodiments the compound of Formula (I) is a racemic compound before the compound of Formula (I) is resolved by the methods disclosed herein. In some embodiments, ee is measured by chiral HPLC.

In some embodiments, the methods of resolving a the compound of Formula (I) described herein, provides the (S)-enantiomer of a compound of Formula (I) an enantiomeric excess of about or at least about 60% ee, about or at least about 65% ee, about or at least about 70% ee, about or at least about 80% ee, about or at least about 85% ee, about or at least about 90% ee, about or at least about 91%, about or at least about 92%, about or at least about 93% ee, about or at least about 94% ee, about or at least about 95% ee, about or at least about 96% ee, about or at least about 97% ee, about or at least about 98% ee, about or at least about 99% ee, about or at least about 99.5% ee, or about or at least about 99.9% ee, including all values therebetween. In some embodiments, the process provides the (S)-enantiomer of a compound of Formula (I) in an enantiomeric excess of about or at least about 80% ee. In some embodiments, the process provides the (S)-enantiomer of a compound of Formula (I) in an enantiomeric excess of a least about 99.5%. In some embodiments, ee is measured by chiral HPLC.

In some embodiments, the methods of resolving a the compound of Formula (I) described herein, provides the (S)-enantiomer of a compound of Formula (I) an enantiomeric excess of from about 60% ee to about 100% ee, including from about 65% ee, about 70% ee, about 80% ee, about 85% ee, about 90% ee, about 91%, about 92%, about 93% ee, about 94% ee, about 95% ee, about 96% ee, about 97% ee, about 98% ee, about 99% ee, about 99.5% ee, about 99.9% ee to about 100% ee, including all subranges therebetween.

In some embodiments, the methods of resolving a the compound of Formula (I) described herein, provides the (R)-enantiomer of a compound of Formula (I) an enantiomeric excess of about or at least about 60% ee, about or at least about 65% ee, about or at least about 70% ee, about or at least about 80% ee, about or at least about 85% ee, about or at least about 85% ee, about or at least about 90% ee, about or at least about 91%, about or at least about 92%, about or at least about 93% ee, about or at least about 94% ee, about or at least about 95% ee, about or at least about 96% ee, about or at least about 97% ee, about or at least about 98% ee, about or at least about 99% ee, about or at least about 99.5% ee, or about or at least about 99.9% ee, including all values therebetween. In some embodiments, the process provides the (R)-enantiomer of a compound of Formula (I) in an enantiomeric excess of about or at least about 80% ee. In some embodiments, the process provides the (R)-enantiomer of a compound of Formula (I) in an enantiomeric excess of a least about 99.5%. In some embodiments, ee is measured by chiral HPLC.

In some embodiments, the methods of resolving a the compound of Formula (I) described herein, provides the (R)-enantiomer of a compound of Formula (I) an enantiomeric excess of from about 60% ee to about 100% ee, including from about 65% ee, about 70% ee, about 80% ee, about 85% ee, about 90% ee, about 91%, about 92%, about 93% ee, about 94% ee, about 95% ee, about 96% ee, about 97% ee, about 98% ee, about 99% ee, about 99.5% ee, about 99.9% ee to about 100% ee, including all subranges therebetween.

NUMBERED EMBODIMENTS OF THE DISCLOSURE

In addition to the disclosure above, the Examples below, and the appended claims, the disclosure sets forth the following numbered embodiments.

1. A process for resolving the (S)- and (R)-enantiomers of a compound of Formula (I):

(I)

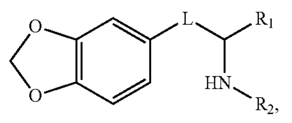

wherein L is a $C_1$-$C_5$ alkylene, carbocyclyl, or heterocyclyl;
$R^1$ is alkyl, benzyl or phenethyl; and
$R^2$ is hydrogen, alkyl, benzyl or phenethyl;
the process comprising:
(a) forming a diastereomeric salt comprising (S)- and (R)-enantiomers of the compound of Formula (I) by mixing the compound of Formula (I) with a chiral acid in a solvent and
(b) resolving the (S)- and (R)-enantiomers of the compound of Formula (I), wherein the enantiomeric excess of the compound of Formula (I) is less than about 50%.

2. A process for resolving the (S)- and (R)-enantiomers of a compound of Formula (I):

(I)

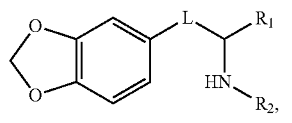

wherein L is a $C_1$-$C_5$ alkylene, carbocyclyl, or heterocyclyl;
$R^1$ is alkyl, benzyl or phenethyl; and
$R^2$ is hydrogen, alkyl, benzyl or phenethyl;
the process comprising:
(a) mixing a compound of Formula (I) and a chiral acid in a solvent to provide a diastereomeric salt of Compound (I) and
(b) resolving the (S)- and (R)-enantiomers of the compound of Formula (I),
wherein the enantiomeric excess of the compound of Formula (I) is less than about 50%.

3. The process of embodiment 1 or 2, wherein the resolving step (b) comprises preferential crystallization of the (S)- or (R)-enantiomer of the compound of Formula (I).

4. The process of embodiment 3, comprising the preferential crystallization of the (S)-enantiomer of the compound of Formula (I).

5. The process of embodiment 3, comprising the preferential crystallization of the (R)-enantiomer of the compound of Formula (I).

6. The process of any of embodiments 1-5, wherein $R^1$ and $R^2$ are methyl.

7. The process of any of embodiments 1-5, wherein $R^1$ is methyl and $R^2$ is hydrogen.

8. The process of any one of embodiments 1-7, wherein L is methylene.

9. The process of any one of embodiments 1-6 or 8, wherein $R^1$ and $R^2$ are methyl and L is methylene.

10. The process of any of embodiments 1-5 or 7-8, wherein $R^1$ is methyl, $R^2$ is hydrogen and L is methylene.

11. The process of any of embodiments 1-10, wherein the solvent is toluene, acetonitrile, methanol, ethanol, isopropanol, dichloromethane, or mixtures thereof.

12. The process of any of embodiments 1-11, wherein the solvent is acetonitrile.

13. The process of any of embodiments 1-12, wherein the mixture of step (a) further comprises an anti-solvent.

14. The process of embodiment 13, wherein the anti-solvent is a heptane or methyl t-butyl ether.

15. The process of any of embodiments 1-14, wherein the step (a) mixture comprises about 0.5 molar equivalents of the chiral acid relative to amount of racemate.

16. The process of any of embodiments 1-15, wherein the step (a) mixture comprises about 1.0 molar equivalent of the chiral acid relative to amount of racemate.

17. The process of any of embodiments 1-16, wherein the chiral acid(S)-2-methoxy-2-phenylacetic acid, L-tartaric acid, dibenzoyl-L-tartaric acid, di-p-toluoyl-L-tartaric acid, L-ascorbic acid, L-aspartic acid, (S)-(+)-mandelic acid, (−)-di-O-isopropyledene-2-keto-L-gulonic acid or (1R, 3S)-(+)-camphoric acid.

18. The process of any of embodiments 1-16, wherein the chiral acid is (R)-2-methoxy-2-phenylacetic acid, D-tartaric acid, dibenzoyl-D-tartaric acid, di-p-toluoyl-D-tartaric acid, D-ascorbic acid, D-aspartic acid, (R)-(−)-mandelic acid, (+)-di-O-isopropyledene-2-keto-D-gulonic acid or (1S, 3R)-(−)-camphoric acid.

19. The process of any of embodiments 1-16, wherein the chiral acid is (S)-2-methoxy-2-phenylacetic acid.

20. The process of any of claims 1-16, wherein the chiral acid is (R)-2-methoxy-2-phenylacetic acid.

21. The process of any of embodiments 1-20, wherein the compound of Formula (I) is a racemate.

22. The process of any of embodiments 3-21, further comprising the step of isolating the preferentially crystallized diastereomeric salt of the compound of Formula (I).

23. The process of embodiment 22, wherein the step of isolating the diastereomeric salt is filtration.
24. The process of embodiment 22 or 23, further comprising combining the crystallized diastereomeric salt and a base to provide enantioenriched free base of the (S)- or (R)-enantiomer of the compound of Formula (I).

EXAMPLES

Compounds of the present disclosure can be synthesized using the following exemplary methods or other methods that are known to those skilled in the art.

General reaction conditions are provided, and reaction products can be purified by known methods including silica gel chromatography using various organic solvents such as hexane, dichloromethane, ethyl acetate, methanol and the like or preparative reverse phase high pressure liquid chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 44th. Ed., Wiley & Sons, 2006, as well as in Jerry March, *Advanced Organic Chemistry,* $4^{th}$ edition, John Wiley & Sons, publisher, New York, 1992 which are incorporated herein by reference in their entirety.

Example 1: Preparation of (R)-3,4-methylenedioxymethamphetamine

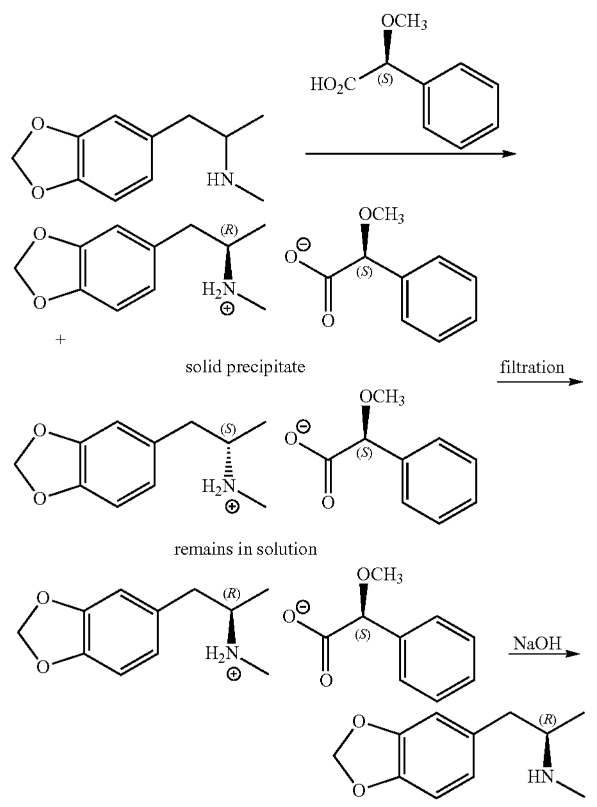

To a stirred solution of rac-MDMA (0.2 g) in acetonitrile (10 mL) at room temperature (22 to 25° C.) was added(S)-alpha-methoxy phenylacetic acid (0.5 eq) and then aged under agitation overnight. The solid precipitate was isolated by filtration to obtain 60 mg of (R)-MDMA (64% yield, and 91.5/8.5 (R/S) enantiomeric ratio as determined by Chiral HPLC analysis). When toluene was used as the solvent, the (R)-MDMA was obtained in 75% yield (of the available) and in 83.8/16.2 enantioselectivity.

The invention claimed is:

1. A process for resolving a diastereomeric salt of one of the (S)- or (R)-enantiomers of a compound of Formula (I):

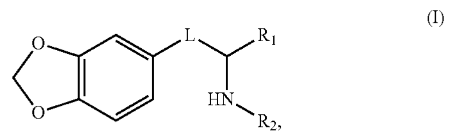

(I)

wherein:

-L- is a $C_1$-$C_5$ alkylene, carbocyclyl, or heterocyclyl;

$R_1$ is -alkyl, -benzyl or -phenethyl; and $R_2$ is -hydrogen, -alkyl, -benzyl or -phenethyl;

the process comprising:

forming a diastereomeric salt of the (S)- and (R)-enantiomer of the compound of Formula (I) by mixing the compound of Formula (I) with a chiral acid in a solvent, wherein the diastereomeric salt of one of the (S)- or (R)-enantiomer of the compound of Formula (I) is preferentially crystallized relative to the diastereomeric salt of the other enantiomer of the compound of Formula (I)

wherein the enantiomeric excess of the compound of Formula (I) is less than about 50%.

2. The process of claim 1, wherein the diastereomeric salt of the (S)-enantiomer of the compound of Formula (I) is preferentially crystallized relative to the diastereomeric salt of the (R)-enantiomer of the compound of Formula (I).

3. The process of claim 1, wherein the diastereomeric salt of the (R)-enantiomer of the compound of Formula (I) is preferentially crystallized relative to the diastereomeric salt of the (S)-enantiomer of the compound of Formula (I).

4. The process of claim 1, wherein $R_1$ and $R_2$ are -methyl.

5. The process of claim 1, wherein $R_1$ is -methyl and $R_2$ is -hydrogen.

6. The process of claim 1, wherein -L- is methylene.

7. The process of claim 1, wherein $R_1$ and $R_2$ are -methyl and -L- is methylene.

8. The process of claim 1, wherein $R_1$ is methyl, $R_2$ is -hydrogen and -L- is methylene.

9. The process of claim 1, wherein the solvent is toluene, acetonitrile, methanol, ethanol, isopropanol, dichloromethane, or mixtures thereof.

10. The process of claim 9, wherein the solvent is acetonitrile.

11. The process of claim 1, further comprising mixing the compound of Formula (I) with an anti-solvent.

12. The process of claim 11, wherein the anti-solvent is a heptane or methyl t-butyl ether.

13. The process of claim 1, comprising mixing about 0.5 molar equivalents of the chiral acid relative to amount of the compound of Formula (I).

14. The process of claim 1, comprising mixing about 1.0 molar equivalent of the chiral acid relative to amount of the compound of Formula (I).

15. The process of claim 1, wherein the chiral acid is (S)-2-methoxy-2-phenylacetic acid, L-tartaric acid, dibenzoyl-L-tartaric acid, di-p-toluoyl-L-tartaric acid, L-ascorbic acid, L-aspartic acid, (S)-(+)-mandelic acid, (−)-di-O-isopropyledene-2-keto-L-gulonic acid, or (1R, 3S)-(+)-camphoric acid.

16. The process of claim 1, wherein the chiral acid is (R)-2-methoxy-2-phenylacetic acid, D-tartaric acid, dibenzoyl-D-tartaric acid, di-p-toluoyl-D-tartaric acid, D-ascorbic acid, D-aspartic acid, (R)-(−)-mandelic acid, (+)-di-O-isopropyledene-2-keto-D-gulonic acid, or (1S, 3R)-(−)-camphoric acid.

17. The process of claim 15, wherein the chiral acid is (S)-2-methoxy-2-phenylacetic acid.

18. The process of claim 16, wherein the chiral acid is (R)-2-methoxy-2-phenylacetic acid.

19. The process of claim 1, wherein the compound of Formula (I) is a racemate.

20. The process of claim 1, further comprising isolating the diastereomeric salt of the (S)- or (R)-enantiomer of the compound of Formula (I).

21. The process of claim 20, further comprising filtration to isolate the diastereomeric salt of the (S)- or (R)-enantiomer of the compound of Formula (I).

22. The process of claim 20, further comprising combining the diastereomeric salt of the (S)- or (R)-enantiomer and a base to provide enantioenriched free base of the (S)- or (R)-enantiomer of the compound of Formula (I).

* * * * *